United States Patent
Jha et al.

(10) Patent No.: US 11,839,495 B2
(45) Date of Patent: Dec. 12, 2023

(54) ELECTRONIC DEVICE FOR MONITORING HEALTH OF EYES OF USER AND METHOD FOR OPERATING THE SAME

(71) Applicant: Samsung Electronics Co., Ltd., Gyeonggi-do (KR)

(72) Inventors: Krishna Kishor Jha, Bangalore (IN); Ashish Kumar Singh, Bangalore (IN); Mahammadrafi Raimansab Maniyar, Bangalore (IN); Vaisakh Punnekkattu Chirayil S B, Bangalore (IN); Rajib Basu, Bangalore (IN); Gaurav Gupta, Bangalore (IN)

(73) Assignee: Samsung Electronics Co., Ltd

( * ) Notice: Subject to any disclaimer, the term of this patent is extended or adjusted under 35 U.S.C. 154(b) by 635 days.

(21) Appl. No.: 16/365,150

(22) Filed: Mar. 26, 2019

(65) Prior Publication Data
US 2019/0290118 A1   Sep. 26, 2019

(30) Foreign Application Priority Data

Mar. 26, 2018 (IN) .......................... 201841011158 PS
Sep. 26, 2018 (IN) ........................ 201841011158 CS

(51) Int. Cl.
*A61B 3/00*    (2006.01)
*A61B 5/00*    (2006.01)
(Continued)

(52) U.S. Cl.
CPC .............. *A61B 5/72* (2013.01); *A61B 3/0008* (2013.01); *A61B 3/0025* (2013.01);
(Continued)

(58) Field of Classification Search
CPC ....... A61B 3/0025; A61B 3/0008; A61B 5/72; G06K 9/00604
See application file for complete search history.

(56) References Cited

U.S. PATENT DOCUMENTS 7,744,216 B1 *   6/2010   Uhlhorn .................. G06F 21/32
                                                           351/204
8,623,081 B2     1/2014   Canovas Vidal et al.
(Continued)

FOREIGN PATENT DOCUMENTS

CN        102068237        5/2011
CN        106663183        5/2017
(Continued)

OTHER PUBLICATIONS

John I. Yellott, A unified formula for light-adapted pupil size, 2012, Journal of Vision, 12(10) 12, 1-16 (Year: 2012).*
(Continued)

*Primary Examiner* — Ephrem Z Mebrahtu
(74) *Attorney, Agent, or Firm* — The Farrell Law Firm, P.C.

(57) ABSTRACT

The embodiments herein disclose methods and systems for monitoring health of eyes of a user, a method includes determining ambient light around an electronic device of the user. On determining that the ambient light is below a pre-defined threshold, the method includes determining a lumen output of at least one content to be displayed in at least one of a continuous manner and at pre-configured intervals. Based on the determined lumen output and at least one user profile, the method includes estimating a variation in a pupil size of the user. Further, the method includes generating an eye health index for the user based on the estimated variation in the pupil size of the user. Further, the method includes tagging the at least one content as safe based on the eye health index for viewing the at least one content.

17 Claims, 24 Drawing Sheets

(51) Int. Cl.
  *G06V 40/19* (2022.01)
  *G06V 10/141* (2022.01)
  *G06V 40/18* (2022.01)
  *G06K 9/00* (2022.01)

(52) U.S. Cl.
  CPC ............ *G06V 10/141* (2022.01); *G06V 40/19* (2022.01); *G06V 40/193* (2022.01)

(56) References Cited

U.S. PATENT DOCUMENTS

| | | | |
|---|---|---|---|
| 9,066,796 | B2 | 6/2015 | Holladay |
| 10,810,773 | B2* | 10/2020 | Yildiz ................ G06V 40/19 |
| 2007/0273611 | A1 | 11/2007 | Torch |
| 2008/0297662 | A1 | 12/2008 | Gibbs |
| 2010/0302507 | A1 | 12/2010 | Desgrosellers et al. |
| 2011/0080421 | A1 | 4/2011 | Capener |
| 2011/0175925 | A1 | 7/2011 | Kane et al. |
| 2011/0205397 | A1 | 8/2011 | Hahn et al. |
| 2011/0270914 | A1* | 11/2011 | Jung ...................... A61B 5/165 709/203 |
| 2012/0057130 | A1 | 3/2012 | Naito |
| 2013/0120390 | A1* | 5/2013 | Marchand ............. G06T 5/006 345/428 |
| 2013/0135196 | A1 | 5/2013 | Park et al. |
| 2013/0229624 | A1 | 9/2013 | Korb et al. |
| 2014/0285436 | A1 | 9/2014 | Wu |
| 2015/0145777 | A1 | 5/2015 | He et al. |
| 2016/0045108 | A1* | 2/2016 | Wu ........................ A61B 3/112 351/210 |
| 2016/0191395 | A1 | 6/2016 | Bao et al. |
| 2016/0232408 | A1 | 8/2016 | Lee et al. |
| 2016/0284095 | A1* | 9/2016 | Chalom ................ G06K 9/627 |
| 2017/0153992 | A1 | 6/2017 | Nair et al. |
| 2017/0277258 | A1 | 9/2017 | Ma et al. |
| 2017/0286745 | A1 | 10/2017 | Chien |
| 2017/0315348 | A1 | 11/2017 | Hayashi |
| 2018/0078445 | A1 | 3/2018 | Bastide et al. |
| 2018/0247611 | A1* | 8/2018 | Carey ...................... G09G 5/30 |
| 2019/0035360 | A1 | 1/2019 | Lee |
| 2020/0036934 | A1* | 1/2020 | Yang ................ H04N 21/44218 |
| 2020/0129063 | A1* | 4/2020 | McGrath ................ G06V 10/82 |
| 2021/0134245 | A1* | 5/2021 | Bonnier ................. G09G 3/001 |
| 2021/0319872 | A1* | 10/2021 | Valentine ............... G16H 40/67 |

FOREIGN PATENT DOCUMENTS

| | | |
|---|---|---|
| CN | 106991792 | 7/2017 |
| CN | 107369431 | 11/2017 |
| CN | 107665696 | 2/2018 |
| JP | 02-102634 | 4/1990 |
| JP | 10-127584 | 5/1998 |
| JP | 2004-097377 | 4/2004 |
| JP | 2010-220942 | 10/2010 |
| KR | 1020130059768 | 6/2013 |
| KR | 1020170015143 | 2/2017 |
| WO | WO 2015/072202 | 5/2015 |
| WO | WO 2017/143091 | 8/2017 |
| WO | WO 2018/022521 | 2/2018 |

OTHER PUBLICATIONS

Tsukahara et al., The relationship between baseline pupil size and intelligence, 2016, Cognitive Psychology, 91, 109-123 (Year: 2016).*
Lee et al., Measuring Eyestrain from LCD TV According to Adjustment Factors of Image; 2009, IEEE, vol. 55, No. 3 pp. 1447-1452 (Year: 2009).*
Samsung, Eye health Monitoring model based on emitted display radiation in VR/Mobile/TV, May 16, 2018, Copyright 2017 SRI-B CTO/IPR Detp. pp. 38.
European Search Report dated Feb. 2, 2021 issued in counterpart application No. 19777308.8-1122, 7 pages.
International Search Report dated Jul. 4, 2019 issued in counterpart application No. PCT/KR2019/003519, 8 pages.
Chinese Office Action dated Feb. 15, 2023 issued in counterpart application No. 201980019345.2, 20 pages.
Chinese Office Action dated Sep. 5, 2023 issued in counterpart application No. 201980019345.2, 10 pages.

* cited by examiner

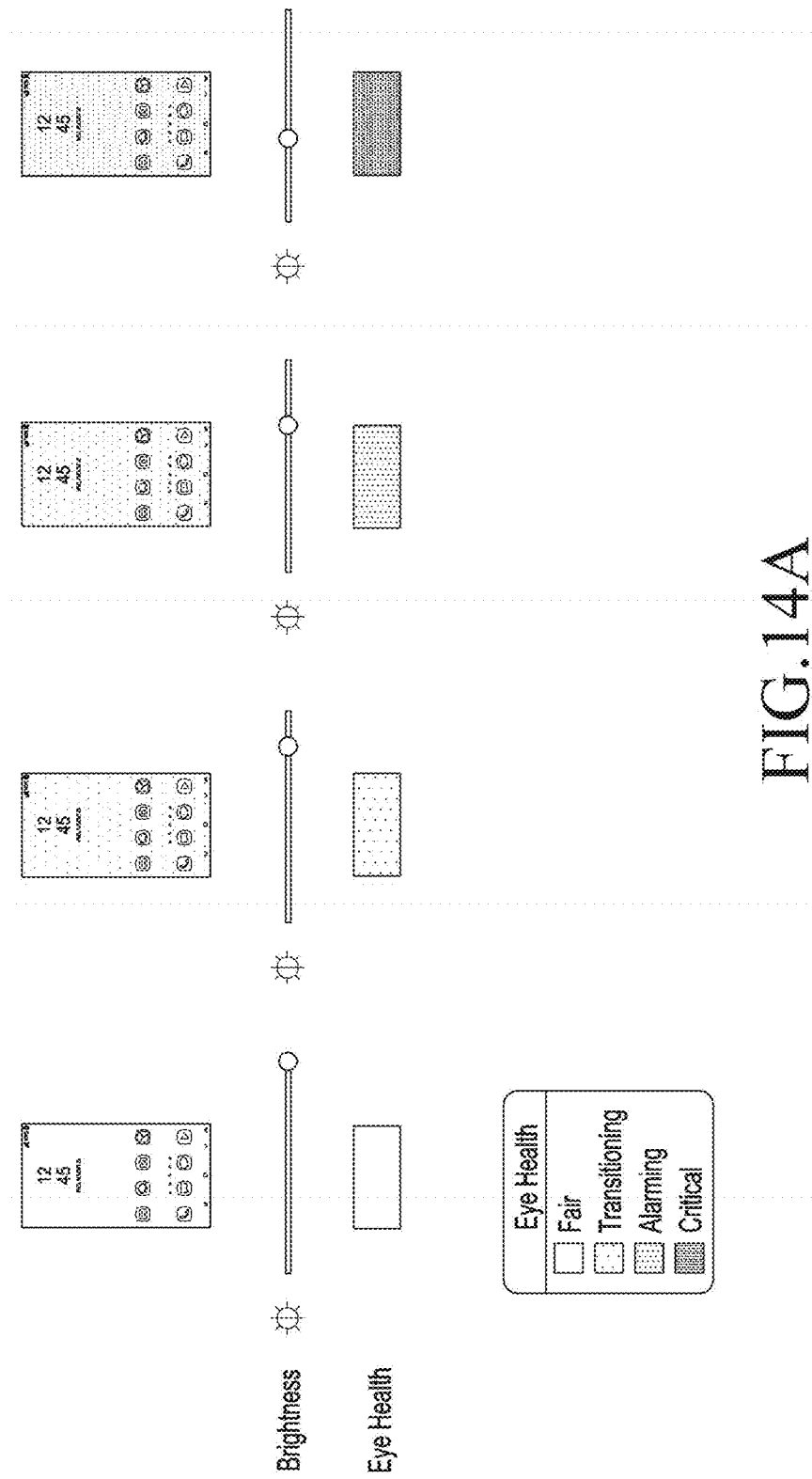

ELECTRONIC DEVICE FOR MONITORING HEALTH OF EYES OF USER AND METHOD FOR OPERATING THE SAME

CROSS REFERENCE TO RELATED APPLICATION

This application is based on and derives the priority of Indian Provisional Application 201841011158 as filed on Mar. 26, 2018, and Indian Complete Application 201841011158 as filed on Sep. 26, 2018, the contents of which are incorporated herein by reference.

BACKGROUND

1. Field

The present disclosure relates generally to eye health monitoring, and more particularly, to monitoring health of the eyes of a user based on contextual display radiation exposure.

2. Description of Related Art

Currently, with the proliferation of electronic display devices (such as mobile phones, smart phones, tablets, computers, laptops, Internet of Things (IoT) devices, wearable computing devices, and so on), content being viewed by the user and the time spent by the user viewing the content has increased significantly. This can lead to asthenopia, also known as eyestrain, eye fatigue, or computer vision syndrome. This can be caused by various reasons such as extended use of electronic devices, strain because of viewing in low light environment, exposure to bright light/glare, long periods of activities that demand focus and concentration, staring continuously on a display in a dark environment, and so on. Symptoms can be dry eyes, difficulty in focusing, sore irritated eyes, headaches, eyes that are slow to focus, excessive tears, increased light sensitivity, and so on.

In conventional approaches, display settings (brightness levels) of an electronic device can be controlled (automatically or manually) based only on ambient light to reduce strain on the eyes of the user.

SUMMARY

The principal object of the embodiments herein is to disclose methods and systems for generating an eye health index for a user based on a total light emitted from an electronic device and a variation in pupil size of the user, wherein the eye health index indicates health status of eyes of the user.

Another object of the embodiments herein is to disclose a method for determining the total light emitted by a display (display radiation) of the electronic device using a lumen model.

Another object of the embodiments herein is to disclose a method for estimating a variation in pupil size of the user based on the display radiation and the user profile.

Another object of the embodiments herein is to disclose a method for controlling configurations/settings of the display based on the eye health index for displaying content.

Another object of the embodiments herein is to disclose a method for tagging the content as safe for viewing the content based on the eye health index.

Another object of the embodiments herein is to disclose a method for providing recommendations to the user based on the eye health index.

Accordingly, the embodiments herein provide methods and systems for monitoring health of eyes of a user. A method herein includes determining ambient light around an electronic device being used by the user. When the determined ambient light is below a pre-defined threshold, the method includes determining a lumen output of at least one content to be displayed by the electronic device in at least one of a continuous manner and at pre-configured intervals. Further, the method includes estimating a variation in a pupil size of the user based on the lumen output and at least one user profile. Based on the estimated variation in the pupil size of the user, the method includes generating the eye health index for the user.

Accordingly, the embodiments herein provide an electronic device for monitoring health of eyes of a user. The electronic device includes a memory, a display module and an eye health-monitoring engine. The eye-health monitoring engine is configured to determine ambient light around the electronic device being used by the user. When the determined ambient light is below a pre-defined threshold, the eye-health monitoring engine is configured to determine a lumen output of at least one content to be displayed by the electronic device in at least one of a continuous manner and at pre-configured intervals. The eye-health monitoring engine is further configured to estimate a variation in a pupil size of the user based on the lumen output and at least one user profile. Based on the estimated variation in the pupil size of the user, the eye-health monitoring engine generates an eye health index for the user.

These and other aspects of the example embodiments herein will be better appreciated and understood when considered in conjunction with the following description and the accompanying drawings. It should be understood, however, that the following descriptions, while indicating example embodiments and numerous specific details thereof, are given by way of illustration and not of limitation. Many changes and modifications may be made within the scope of the example embodiments herein without departing from the spirit thereof, and the example embodiments herein include all such modifications.

BRIEF DESCRIPTION OF THE DRAWINGS

Embodiments herein are illustrated in the accompanying drawings, throughout which like reference letters indicate corresponding parts in the various figures. The embodiments herein will be better understood from the following description with reference to the drawings, in which:

FIGS. 14A and 14B are example diagrams illustrating controlling of brightness settings on an electronic device based on an eye health index, according to embodiments as disclosed herein;

DETAILED DESCRIPTION

Figure 1:
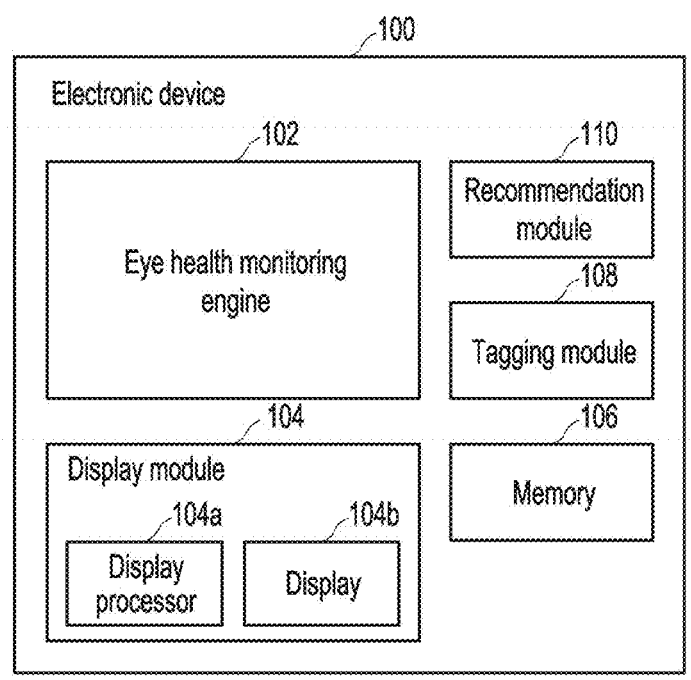
FIG. 1 is a block diagram illustrating various modules of an electronic device for monitoring health of eyes of a user, according to embodiments as disclosed herein.

The example embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The description herein is intended merely to facilitate an understanding of ways in which the example embodiments herein can be practiced and to further enable those of skill in the art to practice the example embodiments herein. Accordingly, this disclosure should not be construed as limiting the scope of the example embodiments herein.

The embodiments herein disclose methods and systems for monitoring health of eyes of a user based on a total light emitted from a display of an electronic device. Referring now to the drawings, and more particularly to FIGS. 1 through 20, where similar reference characters denote corresponding features consistently throughout the figures, there are shown example embodiments.

FIG. 1 is a block diagram illustrating various modules of an electronic device 100 for monitoring health of eyes of a user, according to embodiments as disclosed herein. The electronic device 100 herein refers to a digital device which comprises of at least one display means for displaying content. Examples of the electronic device 100 can be, but is not limited to, a mobile phone, a smartphone, tablet, a phablet, a personal digital assistant (PDA), a laptop, a computer, a wearable device, an IoT (Internet of Things) device, a wearable computing device, a vehicle infotainment system, a medical device, a camera, a television (TV), a Virtual Reality (VR) device, a vehicle display and so on. The content herein refers to at least one of, an image, a video, an animation, text, an application, an icon and so on.

The electronic device 100 includes an eye health-monitoring engine 102, at least one display module 104, a memory 106, a tagging module 108 and a recommendation module 110. In an embodiment, the eye health-monitoring engine 102 can be composed of at least one of a single processer, a plurality of processors, multiple homogenous cores, multiple heterogeneous cores, multiple Central Processing Unit (CPUs) of different kinds and so on. The display module 104 includes a display processor 104a and a display panel/display 104b. In an embodiment, the display 104b may include at least one display means/visual interface suitable for the electronic device 100 and capable of displaying the content to a user. In an embodiment, the display 104b may include at least one of a Liquid Crystal Display (LCD), a Light-Emitting Diode (LED), an Organic Light Emitting Diode (OLED), a Cathode Ray Tube (CRT) display and so on. In an embodiment, the tagging module 108 may be implemented as at least one of a single processer, a plurality of processors, multiple homogenous cores, multiple heterogeneous cores, multiple Central Processing Unit (CPUs) of different kinds and so on. In an embodiment, the recommendation module 110 may be implemented as at least one of a single processer, a plurality of processors, multiple homogenous cores, multiple heterogeneous cores, multiple Central Processing Unit (CPUs) of different kinds and so on. In an embodiment, the eye health-monitoring engine 102, the tagging module 108, and the recommendation module 110 may be implemented using separate one or more hardware device, e.g., a single processer, a plurality of processors, multiple homogenous cores, multiple heterogeneous cores, and multiple CPUs. Alternatively, at least two of the eye health-monitoring engine 102, the tagging module 108, and the recommendation module 110 may be implemented using the same one or more hardware device, e.g., a single processer, a plurality of processors, multiple homogenous cores, multiple heterogeneous cores, and multiple CPUs.

The electronic device 100 may also have access to at least one of the databases (not shown) and the memory 106 for obtaining the content to display. The electronic device 100 may further connect to a server (not shown) using at least one of the Internet, a wired network (a Local Area Network (LAN), Ethernet and so on), a wireless network (a Wi-Fi network, a cellular network, a Wi-Fi Hotspot, Bluetooth, Zigbee and so on) and so on for accessing the content to be displayed to the user. The electronic device 100 may monitor the health of the eyes of the user in response to interactions of the user with the electronic device 100 or at least one of a command, an action, a gesture and so on provided by the user. In an embodiment, a device such as a server (not shown) may be implemented for monitoring the health of the eyes of the user by collecting information from the electronic device 100. In another embodiment, the server can be at least one of a remote server, a cloud server and so on.

The electronic device 100 may also be coupled with devices such as, but not limited to, at least one camera, an iris scanner, a sleep tracking device and so on for monitoring interactions of the user with the electronic device 100, the activities/sleeping patterns of the user and so on. Further, the monitored interaction of the user with the electronic device 100 and the activities of the user can be provided to the eye health-monitoring engine 102.

The eye heath-monitoring engine 102 can be configured to generate an eye health index when ambient light around the electronic device 100 is below a pre-defined threshold. For generating the eye health index, the eye-health-monitoring engine 102 identifies and interprets the light emitted from the display 104*b* (display radiation) of the electronic device 100 over a pre-defined period of time (which can be a long period of time) in different contexts comprising day light, night time, low light, time of day, user age, user health and so on. The eye health-monitoring engine 102 uses a lumen model to identify the total light emitted from display 104*b* of the electronic device 100. Based on the identified total emitted light and a user profile data, the eye health-monitoring engine 102 estimates a variation in pupil size (pupil dilation variance) of the user using a pupil size estimation model. Based on the estimated variation in the pupil size of the user, the user profile and the activities of the user, the eye health-monitoring engine 102 generates the eye health index for the user using an eyestrain model. The eye health index indicates health status of the eyes of the user.

In an embodiment, the eye health-monitoring engine 102 may estimate prospective eyestrain (the eye health index) due to difference between a previous displayed content and a new content to be displayed.

The display processor 104*a* can be configured to control configurations/settings of the display 104*b* based on the eye health index. In an embodiment, the display processor 104*a* may increase/decrease brightness levels of the display 104*b*. In another embodiment, the display processor 104*a* may enable a soothing User Interface (UI)/lighting/color scheme for displaying the content. Thus, strain on the eyes of the user is reduced. The display 104*b* can be configured to display the content on the display 104*b* according to the configurations set by the display processor 104*a*.

The tagging module 108 can be configured to assign a tag for the content for viewing. The tagging module 108 scans content (available across one or more electronic devices/ stored on the electronic device 100) and feeds the content to the eye heath-monitoring engine 102 to generate the eye health index with respect to the scanned contents using the lumen model, the pupil size estimation model and the eyestrain model. The tagging module 108 analyzes the eye health index generated with respect to each scanned content (to be displayed) and assigns the tag for each scanned content for viewing. The tag can be, but is not limited to, a safe tag, an unsafe tag, a pre-defined control range tag and so on. The safe tag indicates that content can be viewed safely in low light. The unsafe tag indicates the possibility of increased eyestrain on viewing the content in the low light. The pre-defined control range tag indicates the requirement of modification in the configurations of the display 104*b* for enabling the user to view the content in the low light with no/minimal eyestrain.

The recommendation module 110 can be configured to provide recommendations to the user based on the eye health index of the user. In an embodiment, the recommendation module 110 recommends at least one of these, but not limited to, media, text, applications, settings/configurations changes, other parameters/content and so on based on the eye health index of the user. In another embodiment, the recommendation module 110 recommends at least one of these, but not limited to, font size(s), color theme(s) and so on based on the eye health index of the user. Thus, the recommendations provided based on the eye health index can reduce the strain on the eyes of the user. In yet other embodiment, the recommendation module 110 suggests device/clinic based eye tests/visit to an ophthalmologist for the user based on the eye health index of the user.

The memory 106 can be configured to store the content, the user profile, information about the display radiation emitted from the electronic device 100 and the pupil size variation, the eye health index of the user and so on. The memory 106 may include one or more computer-readable storage media. The memory 106 may include non-volatile storage elements. Examples of such non-volatile storage elements may include magnetic hard discs, optical discs, floppy discs, flash memories, or forms of electrically programmable memories (EPROM) or electrically erasable and programmable (EEPROM) memories. In addition, the memory 106 may, in some examples, be considered a non-transitory storage medium. The term "non-transitory" may indicate that the storage medium is not embodied in a carrier wave or a propagated signal. However, the term "non-transitory" should not be interpreted to mean that the memory 106 is non-movable. In some examples, the memory 106 can be configured to store larger amounts of information than the memory. In certain examples, a non-transitory storage medium may store data that can, over time, change (e.g., in Random Access Memory (RAM) or cache).

FIG. 1 shows exemplary units of the electronic device 100, but it is to be understood that other embodiments are not limited thereon. In other embodiments, the electronic device 100 may include less or more number of units. Further, the labels or names of the units are used only for illustrative purpose and does not limit the scope of the embodiments herein. One or more units can be combined together to perform same or substantially similar function in the electronic device 100.

Figure 2:
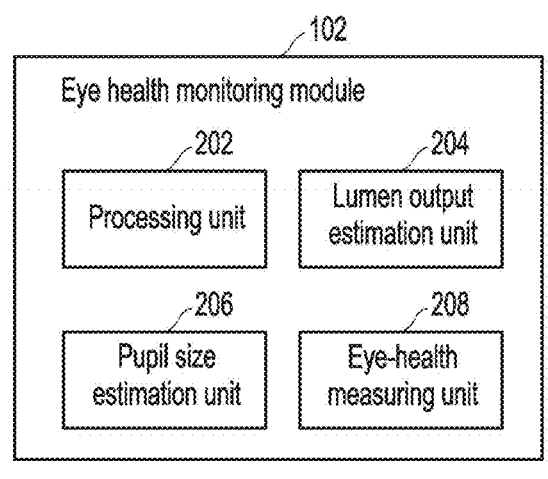
FIG. 2 is a block diagram illustrating various units of a eye health monitoring engine for generating an eye health index, according to embodiments as disclosed herein.

FIG. 2 is a block diagram illustrating various units of the eye health-monitoring engine 102 for generating the eye health index for the user, according to embodiments as disclosed herein. The eye health-monitoring engine 102 includes a processing unit 202, a lumen output estimation unit 204, a pupil size estimation unit 206 and an eye health-measuring unit 208.

The processing unit 202 can be configured to determine an ambient light (ambient lux (luminance) level/ambient light level). The ambient light includes at least one of low/dim light, day light, night time, ambient light and so on. In an embodiment, the processing unit 202 may use an ambient sensor to determine the ambient light. On determining that the ambient light is below a pre-defined threshold (the low light condition), the processing unit 202 calculates histogram data of the content to be displayed. In an embodiment, the processing unit 202 performs periodic sampling of the content to calculate the histogram data of the content. The processing unit 202 also identifies one or more display features of the content (such as color temperature, bit depth, pixel color distribution and so on), a backlight of the display 104b, and a display panel profile (resolution, panel type and so on). The processing unit 202 provides the histogram data, the display features of the content, the backlight and the display panel profile to the lumen output estimation unit 204.

The lumen output estimation unit 204 can be configured to calculate the total light emitted from the display 104b of the electronic device 100 (display radiation/luminance (lumen) output of the content) and a corresponding luminance variance. Embodiments herein use the terms, 'display radiation', 'luminance output of the content', 'total light emitted by the content', 'total luminance' and so on interchangeably and refer to the total light emitted from the display 104b. In an embodiment, the lumen output estimation unit 204 uses the lumen model to calculate the total light emitted from the display 104b. The lumen output estimation unit 204 uses the histogram data, the display features of the content, the backlight and the display panel profile as inputs to the lumen model. The lumen model calculates the total light emitted from the display 104b/total luminance. In an embodiment, the total light emitted from the display 104b is due to a combination of the content (including the display features of the content) on the display 104b and the backlight level (brightness level).

For estimating the total light emitted from the display 104b, the lumen model establishes a relation between sub-pixels of the content and corresponding luminance at the given backlight. The sub-pixels may constitute the pixels of the content, wherein the sub-pixels herein refer to at least one of red, green and blue color. Each sub-pixel may have 256 levels of color. Zero implies black and 255 implies pure color of complete saturation. Initially, the lumen model analyzes 64 colors (4 levels for each sub-pixel and the levels may be obtained by dividing the total range of luminance of the sub-pixel into 3 equal parts) among 16 million colors. In the absence of red sub-pixel, the lumen model observes the luminance behavior of green and blue color (the sub-pixels) as linear. The luminance behavior of green and blue sub-pixels may be represented as:

$$L(0,G,B)=1.002*L(G)+0.748*L(B) \quad (1)$$

wherein, L is the luminance function, G and B are levels of green and blue sub-pixels and the above equation may be obtained from a linear regression of the luminance behavior.

Once the linear relationship for the luminance of the pixel with luminance of green and blue sub-pixels, the lumen model adds red sub-pixel to equation (1) and observes the same linear relationship/luminance behavior. The luminance behavior with the addition of red sub-pixel can be represented as:

$$L(R,G,B)=1.243*L(R)+0.9462*L(0,G,B)=1.234*L(R)+0.948*L(G)+0.708*L(B) \quad (2)$$

Further, the lumen model observes the similar linear relationship or the luminance behavior with the combination of red and blue sub-pixels in the absence of green sub-pixel. The luminance behavior of red and blue sub-pixels can be represented as:

$$L(R,0,B)=1.177*L(R)+1.182*L(B) \quad (3)$$

Even with the addition of green sub-pixel, the lumen model observes the same linear relationship/luminance behavior. The luminance behavior with addition of green sub-pixel can be represented as:

$$L(R,G,B)=0.688*L(R)+0.772*L(G)=0.913*L(G)+1.078*L(R,G,B)=1.269*L(R)+0.913*L(G)+1.274*L(B) \quad (5)$$

Similarly, the lumen model observes the same linear relationship or the luminance behavior for the combination of red and green with the absence of blue sub-pixel. The luminance behavior can be represented as:

$$L(R,G,B)=2.515*L(B)+1.185*L(R,G,0)=0.816*L(R)+0.932*L(G)+2.515*L(B) \quad (6)$$

From the equations 1-6, the lumen model concludes an existence of linear relationship between the luminance of the pixel and the luminance of individual sub-pixels of the content. Thus, the lumen model applies the linear regression with luminance of each sub-pixel as a predictor variable and the luminance of the corresponding pixel as an output variable. Equation obtained for the luminance of each pixel by applying linear regression can be represented as $$L(R,G,B)=1.011*L(R)+0.896*L(G)+2.332*L(B) \quad (7)$$

In an embodiment, the lumen model may use the machine learning based linear regression to find the best fitting line for the output luminance of the pixel for the given luminance values of the sub-pixels.

Further, the pixels present on the content may constitute to the total light emitted by the display 104b. The lumen model calculates the average of the luminance of the pixels present on the content as the total luminance of the content.

The luminance of each pixel can be represented as:

$$L(RGB)=1.072*L(R)+0.9148*L(G)+2.3828*L(B) \quad (8)$$

The luminance of the pixel with red sub-pixel can be represented as:

$$L(R)=0.0007*R^2-0.0223*R+0.5378 \quad (9)$$

The luminance of the pixel with green sub-pixel can be represented as:

$$L(G)=0.0035*G^2-0.1112*G+2.1628 \quad (10)$$

The luminance of the pixel with blue color can be represented as:

$$L(B)=0.0002*B^2-0.0121*B+0.4412 \quad (11)$$

The luminance of the content can be represented as:

$$L(\text{content}) = \frac{(n1*L(p1)+n2*L(p2)+n3*L(p3)+..nn*L(pn))}{(\text{total number of pixels})} \quad (12)$$

wherein, p1, p2, p3 ... pn may be the pixels present in the content and n1, n2, n3 ... nn may be the number of such pixels respectively.

The total light emitted from the display 104b depends on the luminance of the content and the backlight. The total light emitted from the display 104b calculated based on the luminance of the content and the backlight can be represented as:

$$\frac{\left(1.002*\sum_0^{255}(C_{rk}*L(rk))+0.896*\sum_0^{255}(C_{gk}*L(gk))+2.332*\sum_0^{255}C_{bk}*L(bk)\right)}{pixelcount} \quad (13)$$

wherein, $C_{rk}$, $C_{gk}$ and $C_{bk}$ represent count of red, green and blue sub-pixels at level k and L(rk), L(gk) and L(bk) represent luminance values of red, green and blue sub-pixels at a backlight level k.

Also, the lumen model converts the luminance of the content from the various backlight level to the current backlight level of the electronic device 100. For example, consider that the determined backlight level may be 160. The lumen model converts the luminance of the content from the backlight level of 160 to the current backlight level of the electronic device 100. The lumen model formulates a relation between the luminance of the content at different backlight levels. The formulated relation between the luminance of the content at different backlight levels can be represented as:

$$Y = \frac{(\text{luminance of the content at backlight 160})}{\text{luminance at backlight } x} \quad (14)$$

$$Y = 314.9 x^{-1.134} \quad (15)$$

wherein, x may be the current backlight light level of the electronic device 100 and Y may be the dividing factor to determine the required luminance of the content for the backlight level of x.

Further, the total light emitted from the display 104b can be represented as L(content)/Y. Thus, the lumen model uses the combination of the luminance of the content and the backlight to determine the total light emitted from the display 104b.

The pupil size estimation unit 206 can be configured to estimate the variation in the pupil size of the user. In an embodiment, the pupil size estimation unit 206 uses a pupil size estimation model/hierarchical regression model to estimate the variation in the pupil size of the user (the pupil dilation variance). Since, the pupil size depends on adapting luminance, area of adapting field (area of visual fields), age of observer/user, monocular stimulation, binocular stimulation and so on. The pupil size estimation unit 206 provides the determined display radiation and the user profile as input variables to the pupil size estimation model. The user profile can include information such as, but not limited to, user age, an eye profile of the user, an iris scan data and so on. In an embodiment, the iris scan data can be collected using devices such as, an iris scanner, a camera and so on. In an embodiment, the user profile may also include information about the user such as, but not limited to, mental activity, emotional arousal, contrast, recognition, attention and so on.

On receiving the input variables, the pupil size estimation model uses a Holladay formula as a reference for formulating a relation between the input variables and estimates the pupil diameter for the estimated light emitted from the display 104b. The pupil diameter estimated using the Holladay formula can be represented as:

$$D(\text{in mm}) = 7 * \text{Expo}(-0.1007 * L\char`\^0.4) \quad (16)$$

wherein, D represents the estimated pupil diameter and L represents the luminance of the content.

In another embodiment, the pupil size estimation model may consider the area of adapting field (area of visual fields) for estimating the pupil diameter. The pupil diameter estimated using the Holladay formula based on the area of adapting field can be represented as:

$$D(\text{in mm}) = 7.75 - 5.75 * \left[ \frac{\left( \left\{ L * \frac{A}{846} \right\}^{\wedge} 0.41 \right)}{\left( \left\{ L * \frac{A}{846} \right\}^{\wedge} 0.41 + 2 \right)} \right] \quad (17)$$

wherein, D represents the estimated pupil diameter, L represents the luminance of the content and A represents the area of adapting field in $m^2$.

Once the pupil diameter for the determined total light emitted from the display 104b is estimated, the pupil size estimation model calculates the difference between the estimated pupil diameter and the pupil diameter obtained from the user profile. Based on the calculated difference, the pupil size estimation model estimates the variation in the pupil size of the user.

The eye health-measuring unit 208 can be configured to generate the eye health index for the user. In an embodiment, the eye health-measuring unit 208 uses the eyestrain model to generate the eye health index for the user. The eye health-measuring unit 208 provides the determined variation in the pupil size, the user profile, activity data of the user, the display radiation emitted from the electronic device 100 and so on, as input variables to the eyestrain model. The activity data of the user includes information such as, but not limited to, user sleeping patterns, electronic device interaction data and so on. In an embodiment, infrared sensors/front facing cameras of the electronic device 100 can be used to determine the interaction of the user with the electronic device 100. In another embodiment, the display processor 104a can display pop up messages to check the activities of the user with the electronic device 100. In yet other embodiment, the display processor 104a may record gestures (touch, swipe, tap, click, drag and so on) performed by the user on the electronic device 100. In an embodiment, the sensor devices can be used to record the sleeping patterns of the user.

The eyestrain model performs the subjective evaluation of input variables with respect to the estimated variation in the pupil size of the user. Based on the subjective evaluation of the input variables, the eyestrain model generates the eye health index which represents the health status of the eyes of the user (eye health status/eyestrain data). In an embodiment, the eyestrain model generates the eye health index for last 24 hrs which represents the eye strain data for the last 24 hrs. In another embodiment, the eyestrain model generates an overall eye health index which represents the eye strain data from the start of usage of the electronic device 100. In yet other embodiment, the eye health index may vary from level 0 (LVL0) to level 10 (LVL10). The LVL0 represents the minimum eyestrain and the LVL10 represents the maximum eyestrain.

FIG. 2 shows exemplary units of the eye health-monitoring engine 102, but it is to be understood that other embodiments are not limited thereon. In other embodiments, the eye health-monitoring engine 102 may include less or more number of units. Further, the labels or names of the units are used only for illustrative purpose and does not limit the scope of the embodiments herein. One or more units can be combined together to perform same or substantially similar function in the eye health-monitoring engine 102.

Figure 3:
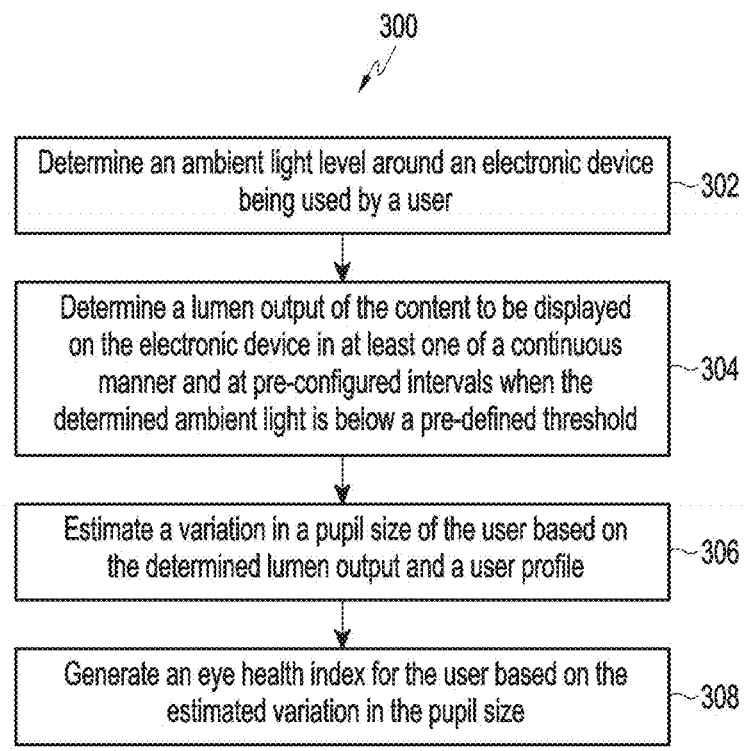
FIG. 3 is a flow diagram illustrating a method for monitoring health of eyes of a user, according to embodiments as disclosed herein.

FIG. 3 is a flow diagram illustrating a method for monitoring the health of the eyes of the user, according to embodiments as disclosed herein.

At step 302, the method includes determining, by the eye health-monitoring engine 102, the level of the ambient light around the electronic device 102 being used by the user. The eye health-monitoring engine 102 can use the ambient sensor to determine the ambient light level.

At step 304, the method includes determining, by the eye health-monitoring engine 102, the lumen output of the content to be displayed (display radiation emitted from the electronic device 100) in at least one of a continuous manner and at a pre-configured interval when the determined ambient light is below the pre-defined threshold. In an embodiment, the eye health-monitoring engine 102 may identify lumen output of at least one content to be displayed on a display of the electronic device (100) at a consistent pre-configured interval. In another embodiment, the interval at which the eye health-monitoring engine 102 identifies lumen output may vary. For example, the interval may be pre-configured as a function of time. In another example, the interval may be pre-configured to be dependent on status of the electronic device, e.g., battery condition, or device temperature. On determining that the ambient light is below the pre-defined threshold, the eye health-monitoring engine 102 determines the histogram data of the content to be displayed, the display features of the content, the backlight of the display 104b, the display panel profile and so on. The eye-health monitoring engine 102 provides the determined histogram data, the display features of the content, the backlight and the display panel profile as the input variables to the lumen model. The lumen model calculates the lumen output of the content to be displayed for the determined ambient light. The lumen model calculates the lumen output based on the luminance of the content and the backlight. For calculating the luminance of the content, the lumen model interprets the pixels and the sub-pixels of the content and establishes the relationship between the sub-pixel (at least one of red, green and blue) level and its corresponding luminance at the determined backlight. Further, the lumen model establishes the relationship between the luminance of combination of the two sub-pixels of the content (at least one of red, green and blue). Thereafter, the lumen model considers the third sub-pixel (at least one of red, green and blue) and establishes the relation for the luminance of the pixel as the function of the individual sub-pixels. The lumen model determines the average of the luminance of all the pixels present in the content to determine the luminance of the content. Further, the lumen model establishes the relationship between the backlight level and the luminance of the content to determine the lumen output of the content/total light emitted from the display 104b. In an embodiment, the lumen model applies the machine learning based linear regression on the input variables to establish the relation for the luminance of the pixel as the function of the individual sub-pixels and the relationship between the backlight level and the luminance of the content. Thus, the lumen output of the content/total light emitted from the display 104b can be calculated based on the RGB (sub-pixels) levels of the content and the backlight level.

At step 306, the method includes estimating, by the eye health-monitoring engine 102, the variation in the pupil size of the user using the lumen output and the user profile. The eye health-monitoring engine 102 provides the calculated lumen output of the content and the user profile to the pupil estimation model for estimating the variation in the pupil size of the user. In an embodiment, the pupil estimation model uses the Holladay formula for estimating the variation in the pupil size of the user based on the variation in the pupil size of the user and the lumen output of the content/total light emitted from the display 104b.

At step 308, the method includes generating, by the eye health-monitoring engine 102, the eye health index for the user based on the estimated variation in the pupil size of the user. The eye health-monitoring engine 102 uses the eye-strain model to generate the eye health index based on the variation in the pupil size of the user, the user profile, the lumen output, and the activities of the user.

The various actions, acts, blocks, steps, or the like in the method and the flow diagram 300 may be performed in the order presented, in a different order or simultaneously. Further, in some embodiments, some of the actions, acts, blocks, steps, or the like may be omitted, added, modified, skipped, or the like without departing from the scope of the invention.

Figure 4:
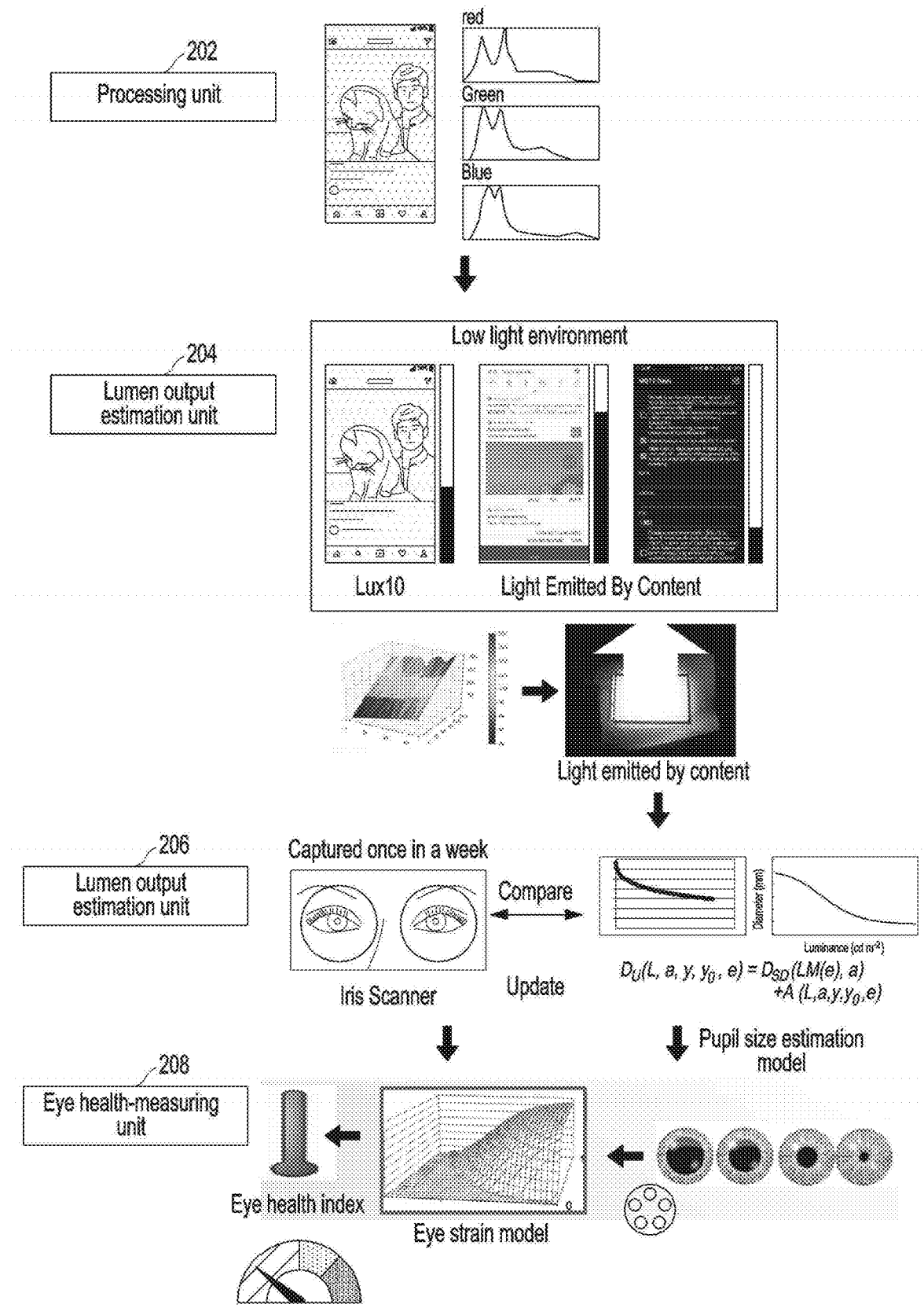
FIG. 4 is an example diagram illustrating generation of an eye health index for a user, according to embodiments as disclosed herein.

FIG. 4 is an example diagram illustrating generation of the eye health index for the user, according to embodiments as disclosed herein. The processing unit 202 of the eye health-monitoring engine 102 calculates the histogram data of the content to be displayed. Based on the histogram data, the lumen output estimation unit 204 of the eye health-monitoring engine 102 determines the total light emitted from the display 104b (lumen output of the content) using the lumen model. The pupil size estimation unit 206 of the eye health-monitoring engine 102 estimates the variation in the pupil size of the user using the pupil size estimation model, the lumen output of the content and the user profile. In an embodiment, the pupil size estimation model can be auto-corrected by taking periodic inputs from the devices such as the iris scanner or the camera coupled to the electronic device 100. Based on the estimated variation in the pupil size of the user, the eye health-measuring unit 208 of the eye health-monitoring engine 102 generates the eye health index using the eyestrain model. In an example herein, the eye health index can be displayed as a needle on a semi-circular chart.

Figure 5:
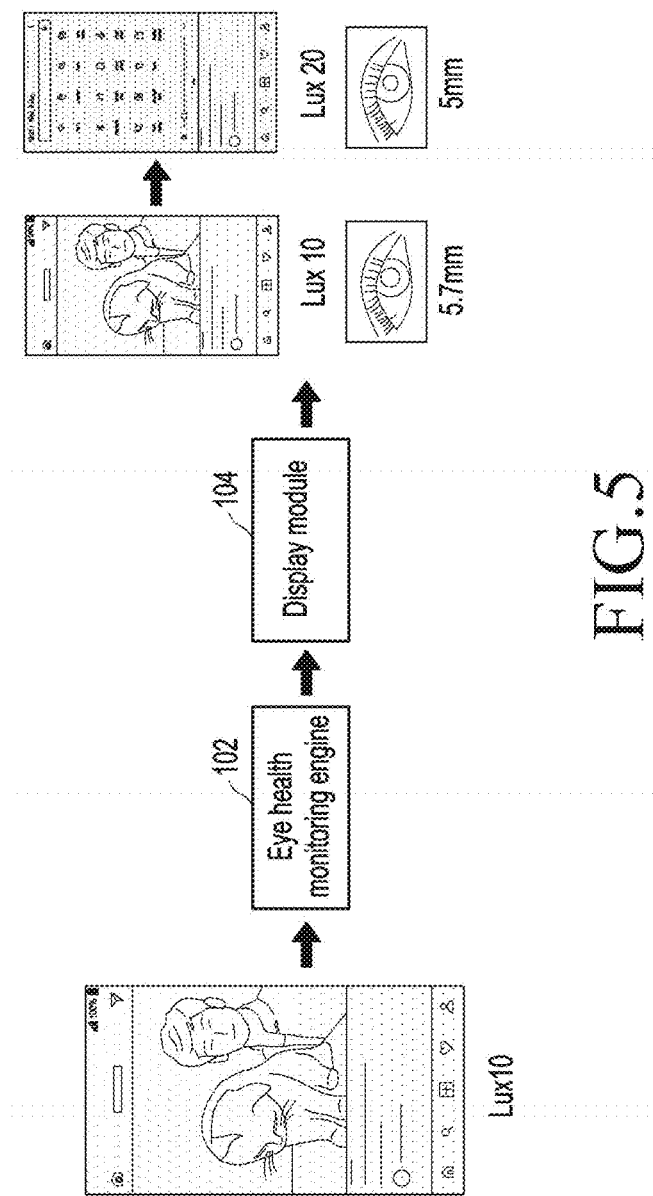
FIG. 5 is an example diagram illustrating display of content based on an eye health index, according to embodiments as disclosed herein.

FIG. 5 is an example diagram illustrating the content being displayed based on the eye health index, according to embodiments as disclosed herein. Embodiments herein enable the eye health-monitoring engine 102 to determine the lumen output of the content based on the histogram data in the low light level condition. For example, the lumen output of the content to be displayed can be LUX 10. Further, the eye health-monitoring engine 102 estimates the variation in the pupil size of the user based on the lumen output of the content. Based on the estimated variation in the pupil size of the user, the eye-health monitoring engine 102 estimates the eye health index for the user. The display processor 104a regulates the brightness level of the display 104b based on the eye health index. For example, consider that the eye health index transitions due to a change of 0.7 mm (from 5.7 mm to 5 mm) in the pupil size. Based on the eye health index, the display processor 104a performs transition of dark to white content by increasing the brightness of the display 104b such that the lumen output of the content may be increased to LUX 20. Thus, the transition of the dark to white content may reduce the strain on the eyes of the user (or headache) and may provide a soothing effect to the eyes of the user.

Figure 6:
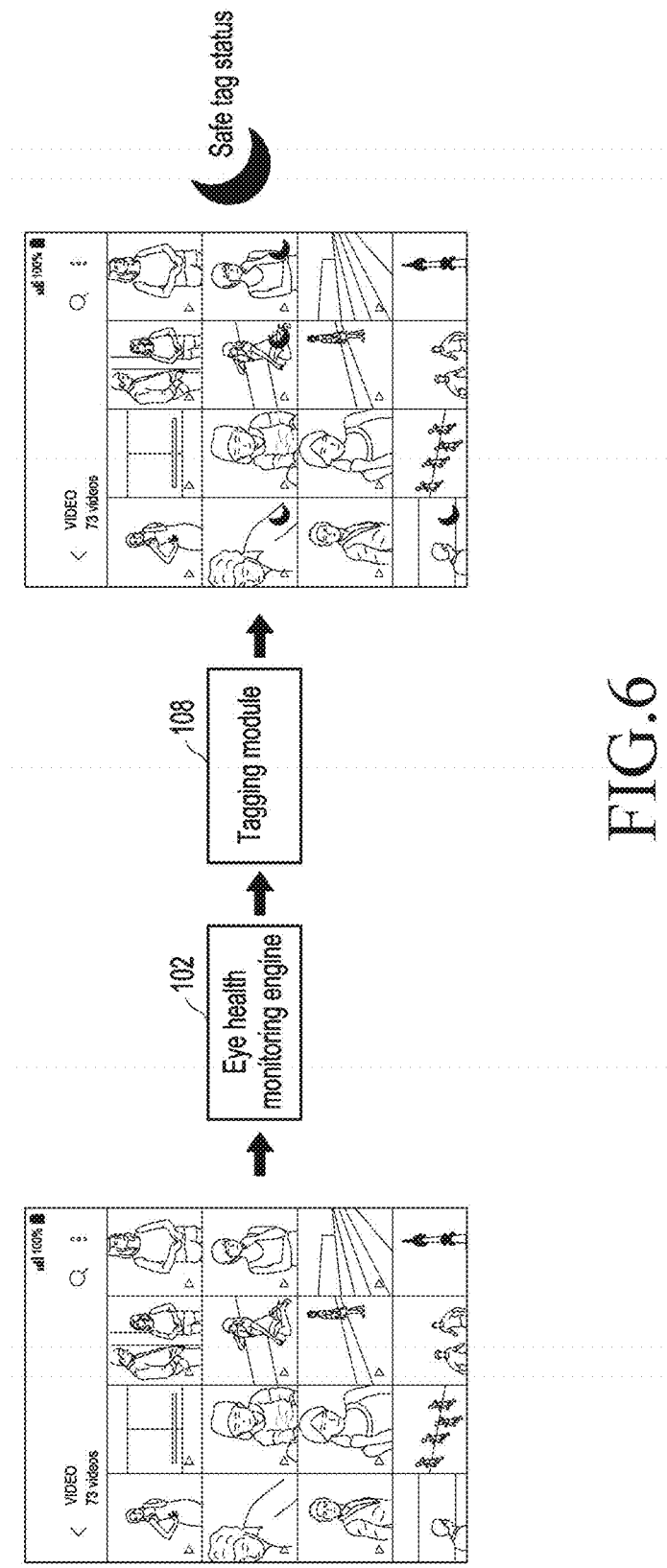
FIG. 6 is an example diagram illustrating tagging of content based on an eye health index as safe for viewing, according to embodiments as disclosed herein.

FIG. 6 is an example diagram illustrating tagging of the contents based on the eye health index as safe for viewing, according to embodiments as disclosed herein. Embodiments herein scan and analyze the videos/contents stored on the memory 106 for probable viewing. The eye health-monitoring engine 102 estimates the pupil dilation variance (the variation in the pupil size of the user) for a period required for viewing the content by applying the lumen model and the pupil size estimation model. Based on the estimated pupil dilation variance, the eye health-monitoring engine 102 generates the eye health index using the eyestrain model. The tagging module 108 can tag the content as safe/unsafe for low light viewing based on the eye health index. For example, the safe tag is assigned for the videos as illustrated in FIG. 6 for viewing the videos in the low light condition.

Figure 7:
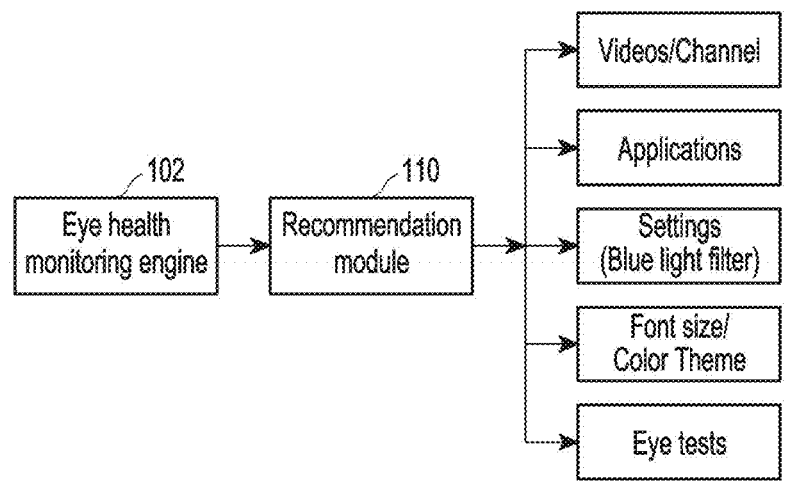
FIG. 7 is an example diagram illustrating providing of recommendations to a user based on an eye health index, according to embodiments as disclosed herein.

FIG. 7 is an example diagram illustrating providing of the recommendations to the user based on the eye health index, according to embodiments as disclosed herein. Embodiments herein enable the eye health-monitoring engine 102 to generate the eye health index for the user based on the display radiation emitted from the electronic device 100. Based on the generated eye health index, the recommendation module 110 recommends at least one of the content/videos/channels, the applications, the configuration/setting changes, the font size/color theme, brightness, and so on for reducing the strain on the eyes of the user. Also, the recommendation module 110 can provide suggestions for the user for device/clinic based eye tests, visiting the ophthalmologist and so on.

Figure 8A:
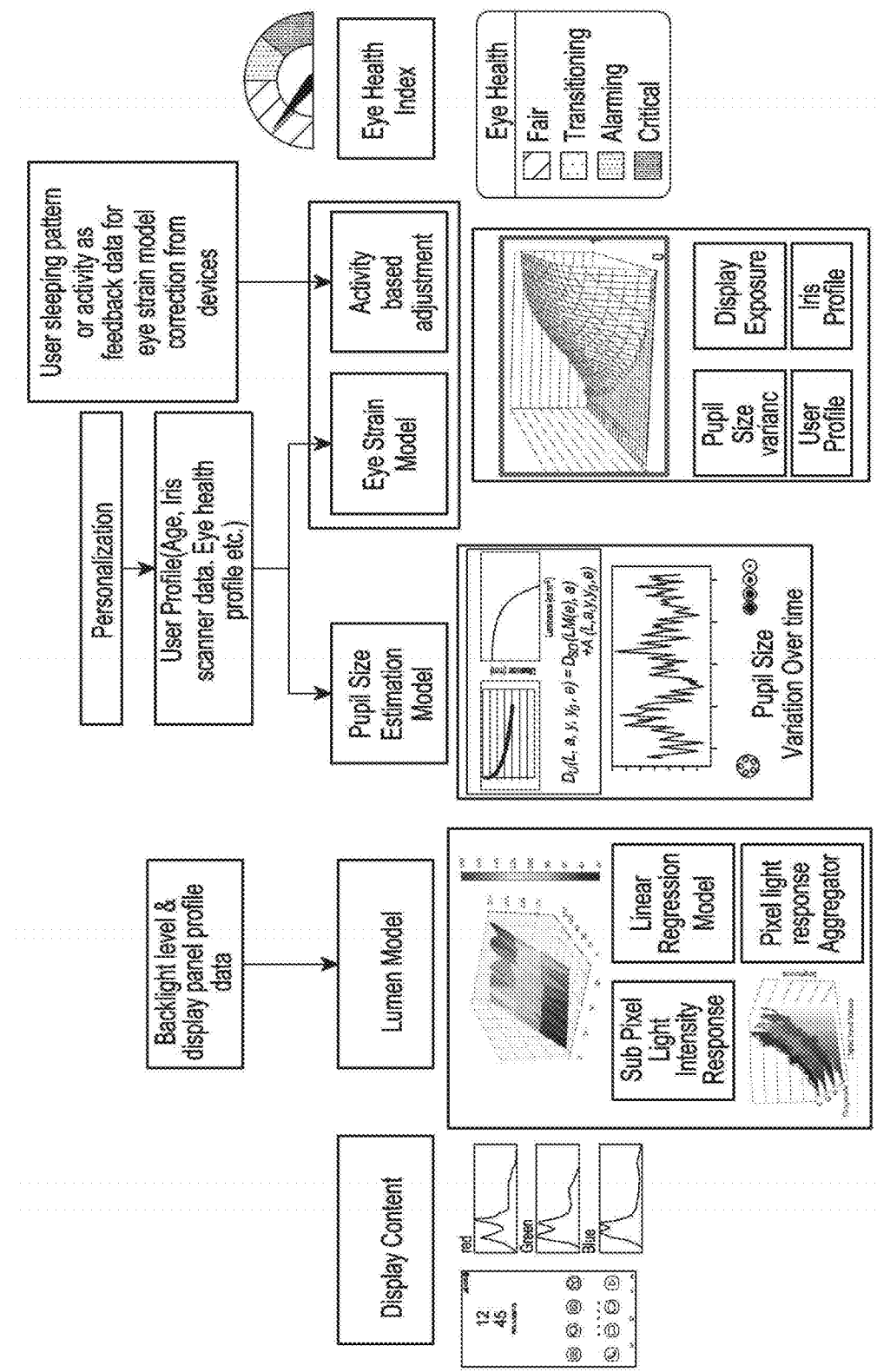
FIGS. 8A and 8B are example diagrams illustrating monitoring of health of eyes of a user, according to embodiments as disclosed herein.
Figure 8B:
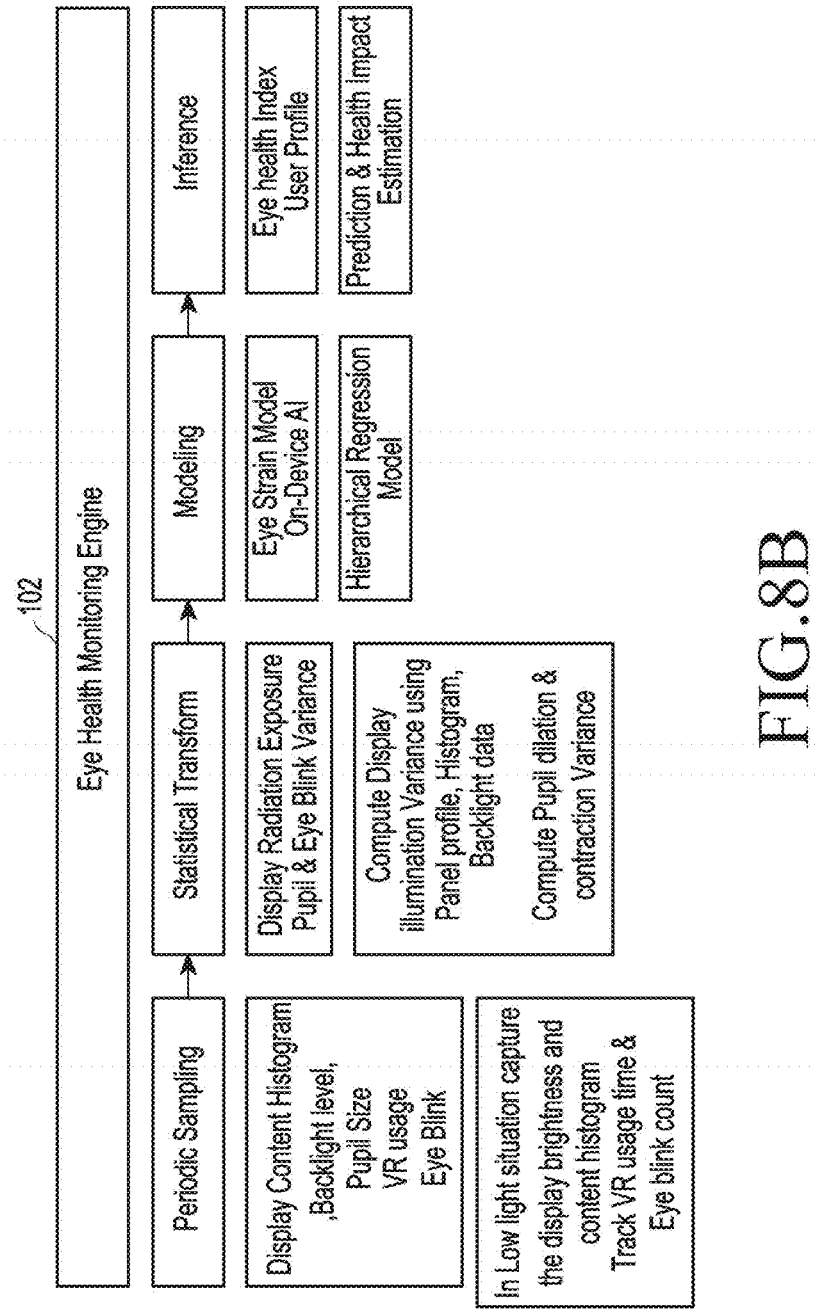

FIGS. 8A and 8B are example diagrams illustrating monitoring of the health of the eyes of the user, according to embodiments as disclosed herein.

FIG. 8A illustrates an example diagram illustrating generation of the eye health index. As illustrated in FIG. 8A, the eye health-monitoring engine 102 performs the periodic sampling of the content to be displayed and calculates the histogram data of the content to be displayed. The eye health-monitoring engine 102 calculates the lumen output of the content (display radiation/total display light) using the lumen model. The lumen model receives information such as, but not limited to, the histogram data, the ambient light around the electronic device 100, the display panel profile and so on to calculate the lumen output. Based on the received information, the lumen model determines the sub-pixel light intensity response and applies the linear regression on the determined sub-pixel light intensity response to predict the linear model. The linear model predicts the aggregation of the pixel light response/lumen output.

Further, the eye health-monitoring engine 102 uses the pupil size estimation model to estimate the variation in the pupil size of the user. The pupil size estimation model estimates the variation in the pupil size of the user based on the lumen output and the user profile (the user age, the iris scan data, the eye health profile and so on). Based on the estimated variation in the pupil size of the user, the eye health-monitoring engine 102 uses the eyestrain model to generate the eye health index. The eyestrain model uses the estimated variation in the pupil size of the user, the lumen output, the user profile and the activities of the user to calculate the eye health index. In an embodiment, the eyestrain model can be corrected using at least one of the activities of the user (the sleeping patterns, the inputs/feedbacks from the devices such as an iris scanner, a camera and so on) to generate the eye health index. In an example herein, the eye health index can include the health status of the eyes of the user such as, but not limited to, a fair status, a transitioning status, an alarming status, a critical status and so on. Based on the eyestrain data/eye health index over a period of time, the eye health-monitoring engine 102 can provide two eye health index metrics to the user (last 24 hours eye health index and overall eye health index). In addition, the eye health-monitoring engine 102 can provide the user with instantaneous eyestrain data.

FIG. 8B depicts the eye health-monitoring engine 102 for monitoring the health of the eyes of the user. As illustrated in FIG. 8B, the eye health-monitoring engine 102 initially performs the periodic sampling of the display content histogram, backlight level of the display, pupil size, VR usage, eye blink rate, display brightness and content histogram (in low light situations), and so on.

The eye health-monitoring engine 102 then statistically transforms the sampled data which comprises of determining the display radiation emitted from the display panel 104*b*, the pupil and eye blink variance. The eye health-monitoring engine 102 can compute the luminance variance using the display panel profile, the histogram and the backlight data. The eye health-monitoring engine 102 computes the pupil dilation and contraction variance. Further, the eye health-monitoring engine 102 performs modeling of the eyestrain using the hierarchical regression model which can involve a self-correcting technique with a processed sampled dataset. Then, the eye health-monitoring engine 102 predicts the health of the eyes (the eye health index) of the user considering the user profile.

Figure 9A:
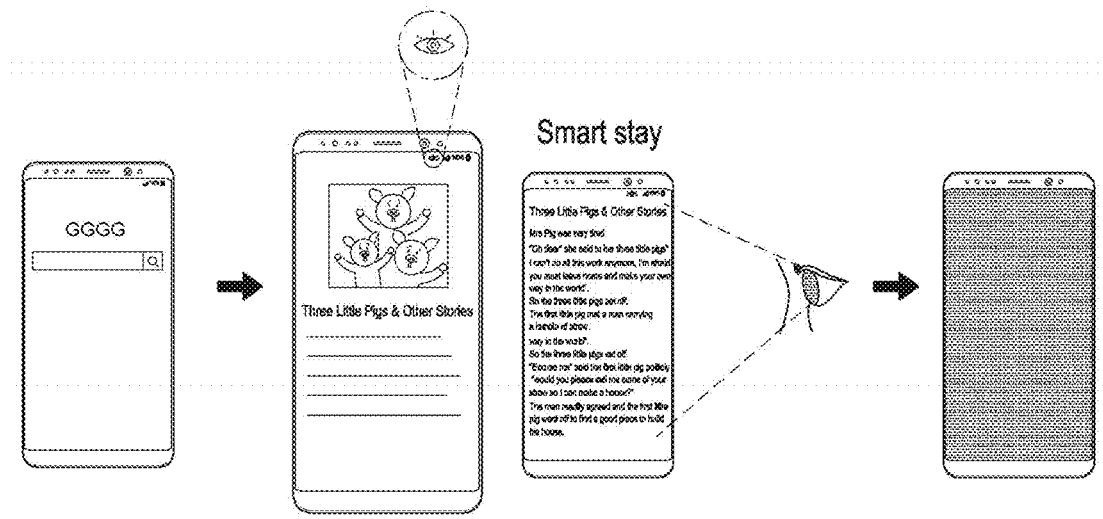
FIGS. 9A, 9B, 9C and 9D are example diagrams illustrating recording of activities of a user for monitoring health of eyes of the user, according to embodiments as disclosed herein.
Figure 9B:
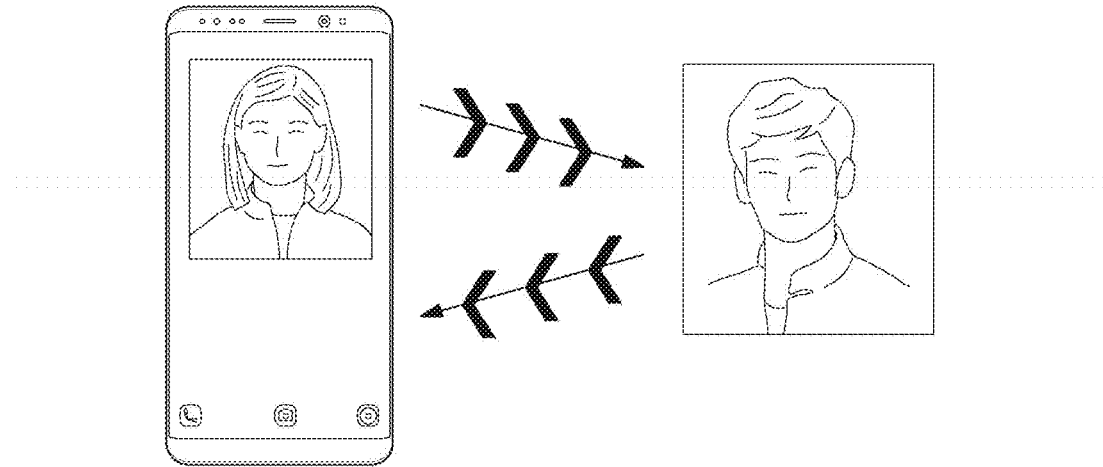
Figure 9C:
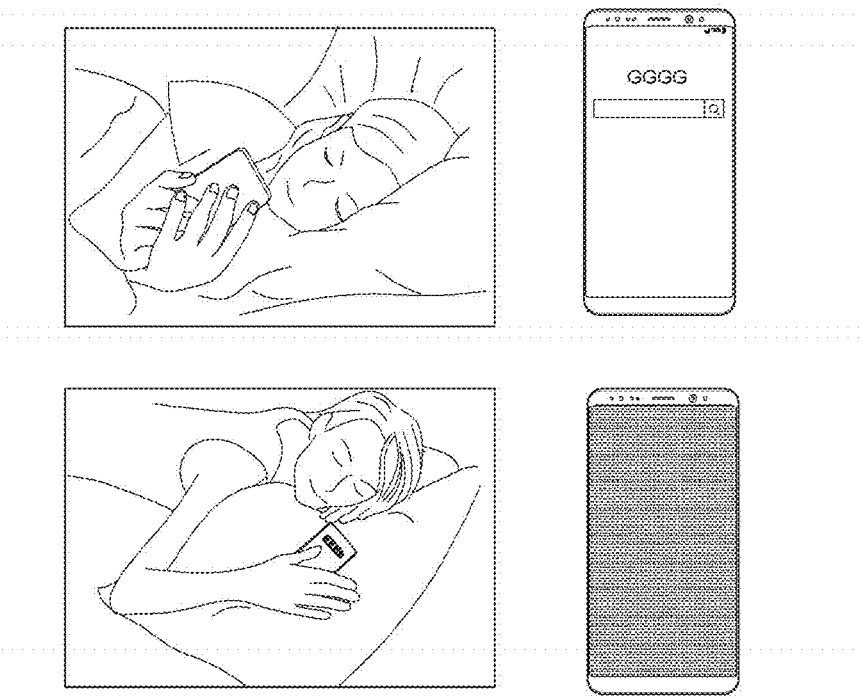
Figure 9D:
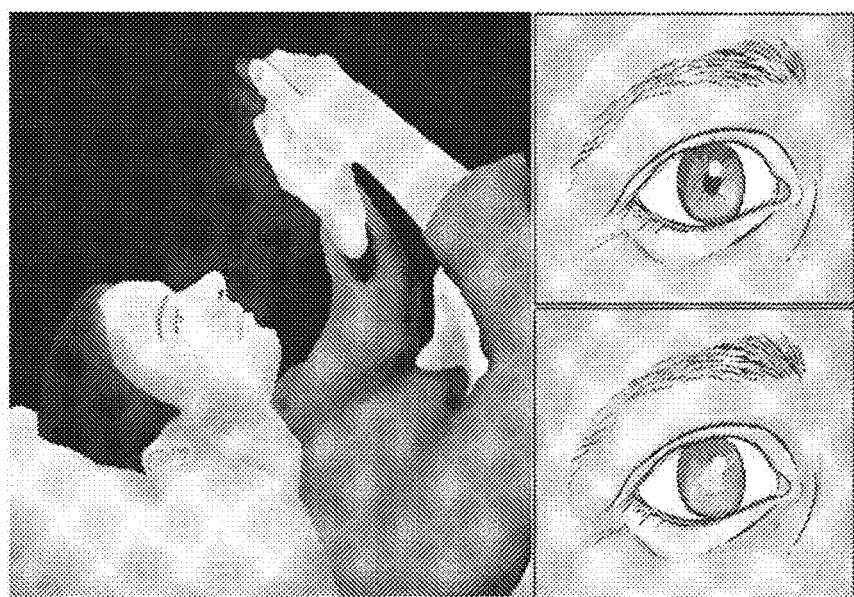

FIGS. 9A, 9B, 9C and 9D are example diagrams illustrating recording of the activities of the user for monitoring the health of the eyes of the user, according to embodiments as disclosed herein. In an example embodiment, the front camera of the electronic device 102 can be enabled to determine whether the user is watching the display content (recording the activities of the user). When no user activity is detected, embodiments herein turn off the electronic device 102 as illustrated in FIG. 9A. In another embodiment, the infrared sensors can be used to detect the presence of the user near the electronic device 100 as illustrated in FIG. 9B. In yet other embodiment, the sleep tracking devices can be used to track the sleeping patterns of the users as illustrated in FIGS. 9C and 9D. In addition, the pop up messages can be displayed to the user to check the user activeness with the electronic device 100. Also, the last gestures (touch, drag, click, tap and so on) performed on the electronic device 100 can be recorded. Thus, embodiments herein use at least one of the cameras of the electronic device 100, the infrared sensors, the sleep tracking devices and so on to determine the activities of the user. The activities of the user can be, but not limited to, a period for which the user is looking at the content displayed on the electronic device 100, usage of the electronic device 100 by the user in night with dim or no light, usage of the electronic device 100 by the user by keeping the electronic device 100 too close to eyes and so on. Thus, the recorded user activities can be used for predicting the health status of the eyes of the user.

Figure 10:
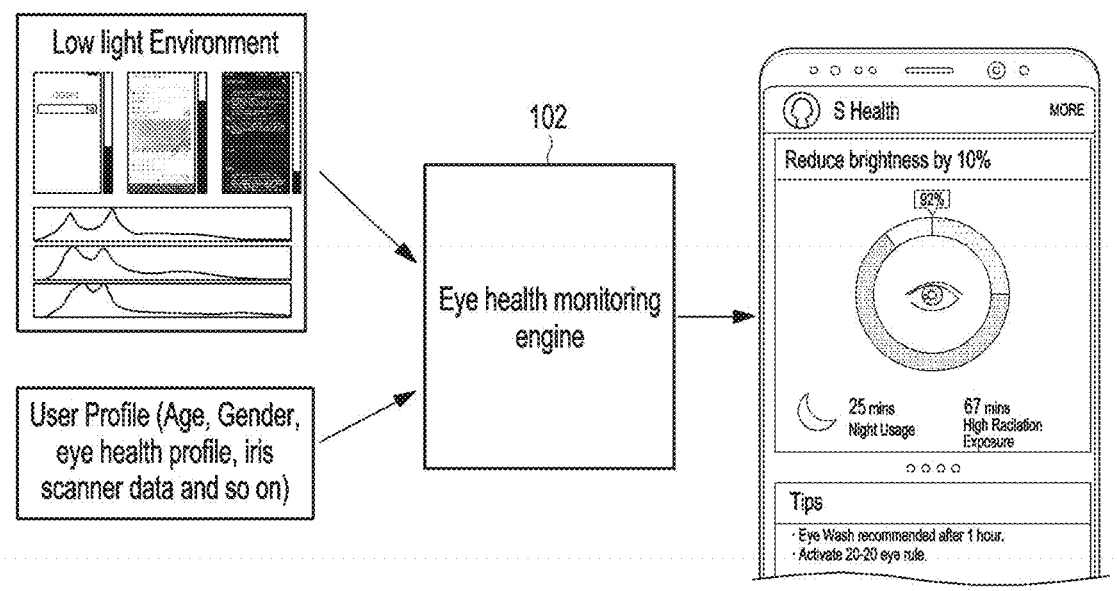
FIG. 10 illustrates an example use case, wherein an eye health status, suggestions and recommendations are displayed on an application resident on an electronic device, according to embodiments as disclosed herein.

FIG. 10 illustrates an example use case, wherein an eye health status, suggestions and recommendations are displayed on an application resident on the electronic device 100, according to embodiments as disclosed herein. Embodiments herein enable the eye health-monitoring engine 102 to predict the eye health status based on the sampled ambient light level around the electronic device 100, the display radiation profile, the user profile and so on. Based on the predicted eye health status, the recommendation module 110 can display the health status of the eyes, the suggestions/tips, the recommendations to the user. Thus, the strain on the eyes can be reduced.

Figure 11:
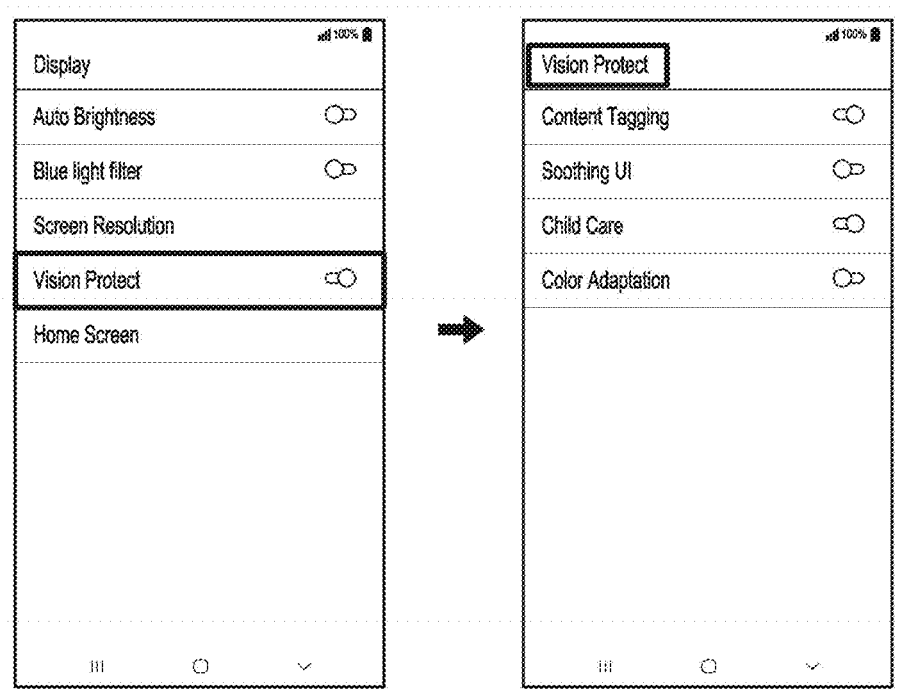
FIG. 11 illustrates example use case for providing a vision protect mode, according to embodiments as disclosed herein.

FIG. 11 illustrates an example use case for providing a vision protect mode, according to embodiments as disclosed herein. Embodiments herein provide the vision protect mode in order to enable at least one feature such as, but not limited to, a content tagging feature, a soothing UI feature, a child care feature, a color adaption feature and so on present on the electronic device 100 based on the eye health index. When the content tagging feature is enabled, the tagging module 108 can assign the contents present on the electronic device with the tag for safe viewing. The tag can be shown in the application based on the ambient light (such as night/day/ambient light, and so on). The tag can be a dynamic tag with colors being used to show strength of prospective strain. When the soothing UI feature is enabled, the display processor 104a can enable the soothing UI based on the eye health index which further provides soothing to the eyes of the user. When the child care feature is enabled, the display processor 104a can adjust the display controls by monitoring child exposure to the display radiation to reduce eye health impact. When the color adaption feature is enabled, the display processor 104a recommends a text color and background color to the user to reduce the strain on the eyes of the user.

Figure 12:
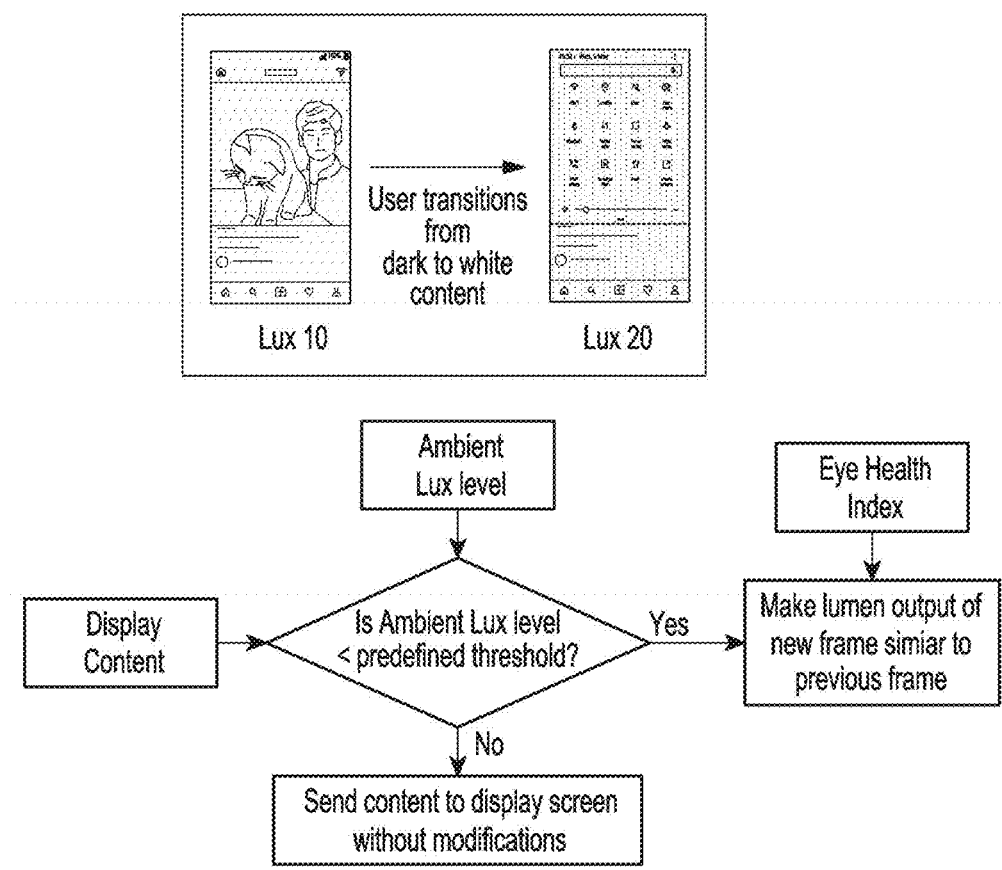
FIG. 12 illustrates an example use case for enabling a soothing User Interface (UI) based on an eye health index, according to embodiments as disclosed herein.

FIG. 12 illustrates an example use case for enabling the soothing UI based on the eye health index, according to embodiments as disclosed herein. Embodiments herein provide the ambient light, the content to be displayed and the previously generated eye health index as inputs to the eye health-monitoring engine 102. The eye-health monitoring engine 102 compares the ambient light with a pre-defined threshold for displaying the content. When the ambient light is greater than the pre-defined threshold, the eye health-monitoring engine 102 provides the content to the display 104b for displaying the content without any modifications.

When the ambient light level is lesser than the pre-defined threshold, the eye health-monitoring engine 102 instructs the display processor 104a to make a lumen output of a new frame similar to a previous frame using the lumen model applied on the received inputs. As illustrated in FIG. 12, based on the eye health index, the soothing UI can be enabled to perform transition from the dark content to the white content (the luminance can be changed to LUX 20). Thus, the eye light adaption effort can be eliminated which can occur due to change in content/display. In addition, enablement of the soothing UI provides the soothing to the eyes of the user and reduces headache/strain.

Figure 13:
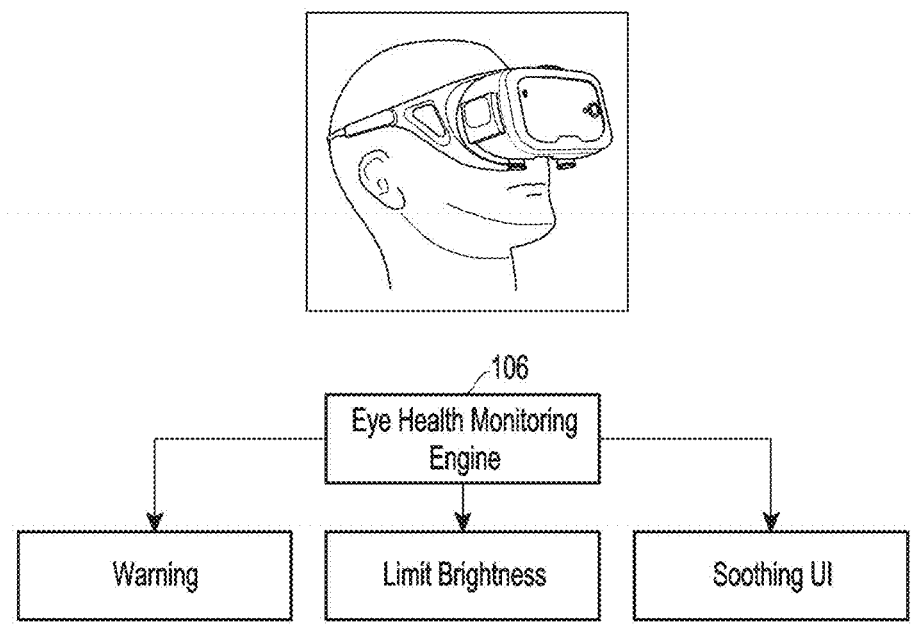
FIG. 13 illustrates an example use case for providing warnings related to usage of a Virtual Reality (VR) device and capping brightness in the VR device and enabling a soothing UI based on an eye health index, according to embodiments as disclosed herein.

FIG. 13 illustrates an example use case for providing warnings related to usage of the Virtual Reality (VR) device 100 (the electronic device 100) and capping brightness in the VR device and enabling the soothing UI based on the eye health index, according to embodiments as disclosed herein. Embodiments herein enable the eye health-monitoring engine 102 to monitor the eyestrain resulting from continuous usage of the VR device 100. In an embodiment, based on the monitored eyestrain, the recommendation module 110 can show warnings to the user. In another embodiment, based on the monitored eyestrain, the display processor 104a can limit the brightness in the VR device 100. In yet other embodiment, based on the monitored eyestrain, the display processor 104a can enable soothing UI which eliminates eye light adaption effort occurring due to change in content.

Figure 14B:
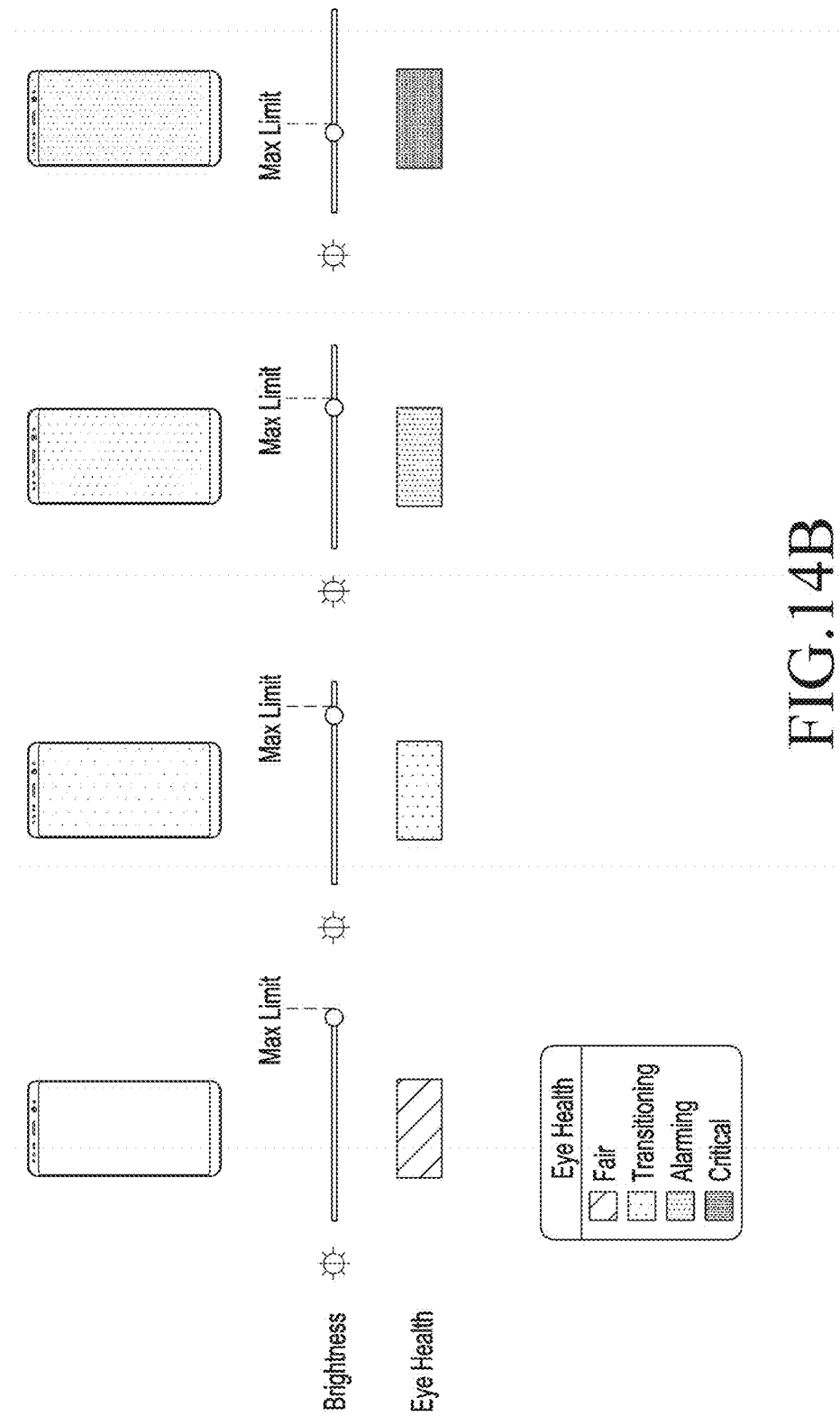

FIGS. 14A and 14B are example diagrams illustrating controlling of brightness settings on the electronic device 100 based on the eye health index, according to embodiments as disclosed herein. The eye health-monitoring engine 102 adjusts the brightness of the display panel 104b based on the eye health index as illustrated in FIG. 14A. Also, the eye health-monitoring engine 102 determines a maximum brightness cap based on the eye health index as illustrated in FIG. 14B. The brightness cap may be applicable to both manual and auto brightness settings. Thus, determining the maximum brightness cap and adjusting the brightness can prevent further degradation in the eye health of the user.

Figure 15A:
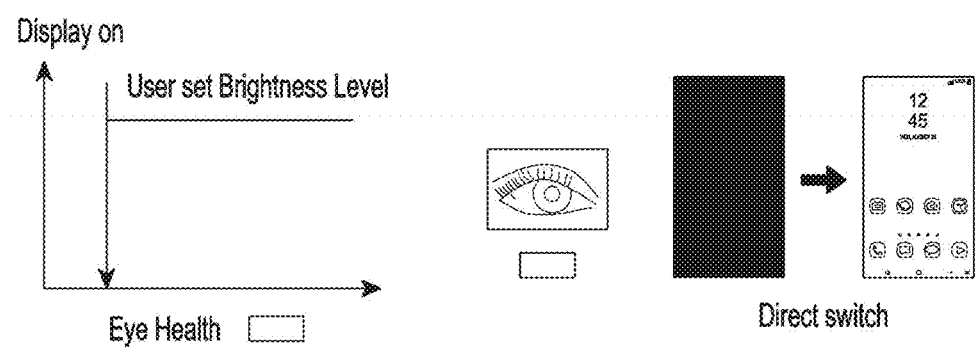
FIGS. 15A and 15B are example diagrams illustrating controlling of glare emitted from an electronic device based on an eye health index, according to embodiments as disclosed herein.
Figure 15B:
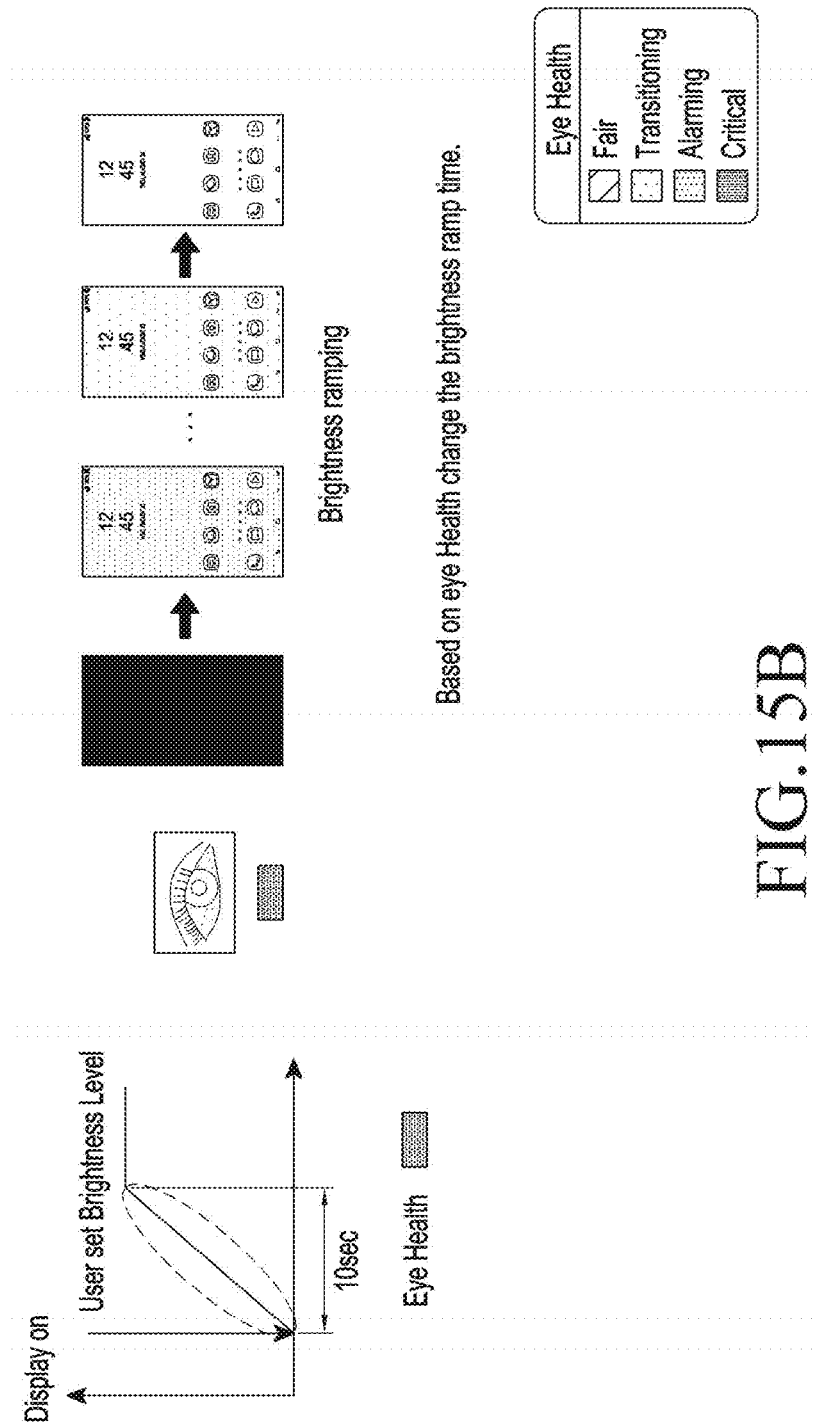

FIGS. 15A and 15B are example diagrams illustrating controlling of glare emitted from the electronic device 100 based on the eye health index, according to embodiments as disclosed herein. A sudden turning ON of the electronic device 100 produces a glare which irritates the user in the low light condition. In this case, the display processor 104a can moderate the display light based on the health status of the eyes of the user. Consider a scenario as illustrated in FIG. 15A, wherein the eye health status of the user is fair. The display module 104 can display the content without regulating the display settings (so the brightness ramp time is negligible). Thus, there may be a direct switch from the OFF state of the electronic device 100 to the ON state without any modifications.

Consider another scenario as illustrated in FIG. 15B, wherein the eye health status of the user is critical. The calculated brightness ramp for the critical eye health may be 10 seconds. Thus, the display module moderates the display light instead of directly switching from OFF state of the electronic device 100 to the ON state. Thus, the glare produced from the sudden turning ON of the electronic device 100 can be controlled which further reduces the strain on the eyes of the user.

Figure 16:
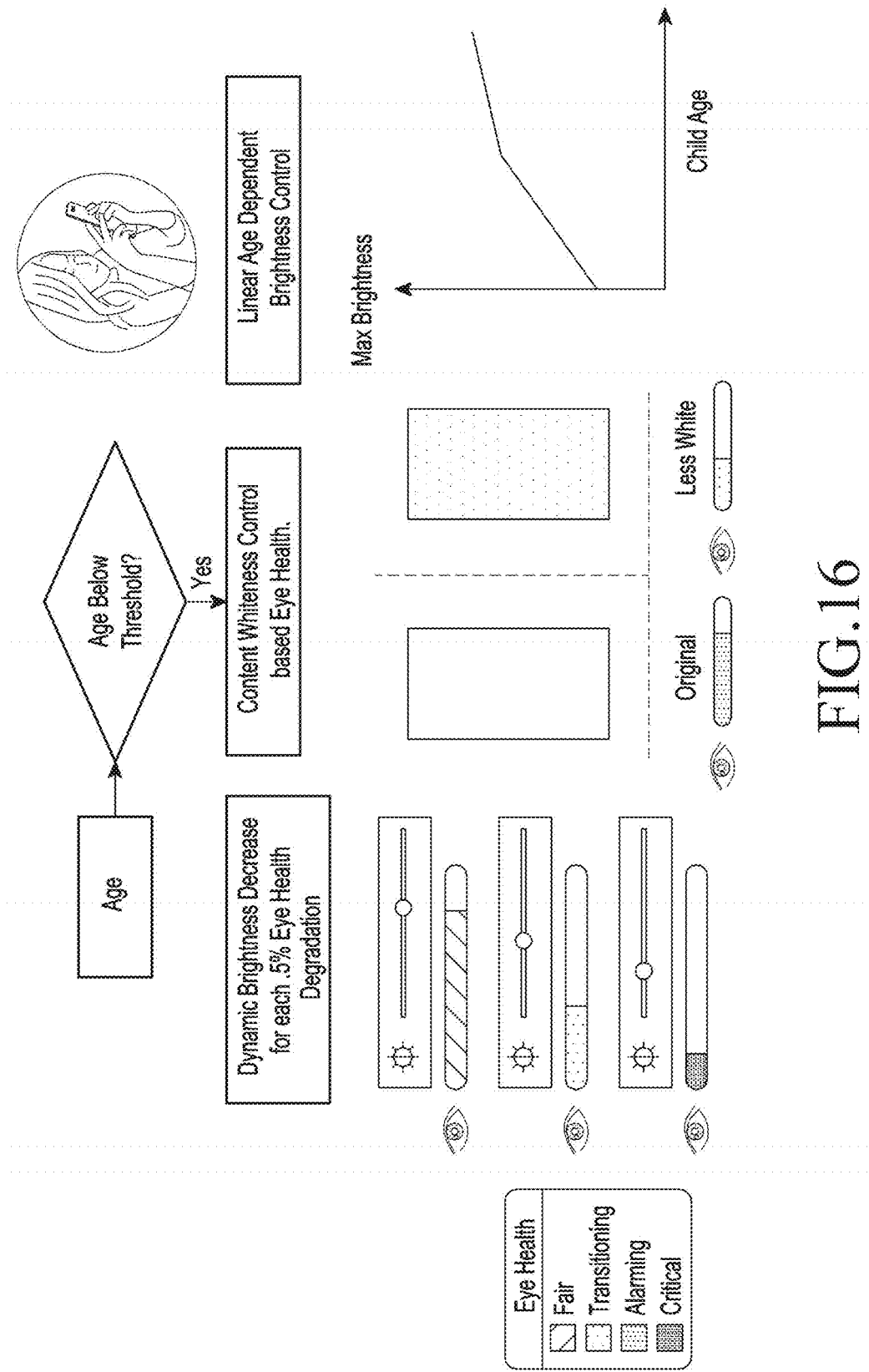
FIG. 16 illustrates an example use case of a child care mode based on an eye health index, according to embodiments as disclosed herein.

FIG. 16 illustrates an example use case of the child care mode based on the eye health index, according to embodiments as disclosed herein. The eye health-monitoring engine 102 can estimate the age of the user. In an embodiment, the eye health-monitoring engine 102 can use inputs from at least one of the iris scanner, the camera and so on for estimating the age of the user. The eye health-monitoring engine 102 compares the estimated age with a pre-defined threshold. On determining that the estimated age is below the pre-defined threshold, the eye health-monitoring engine 102 identifies the user as a child and monitors the child exposure to the display radiation. Based on the monitored child exposure to the display radiation, the eye health-monitoring engine 102 generates the eye health index. Based on the eye health index, the display processor 104a can adjust the display controls to reduce eye health impact. The display controls can be at least one of content whiteness control, linear age dependent brightness control, dynamic brightness decrease for each 5% eye health degradation and so on.

Figure 17:
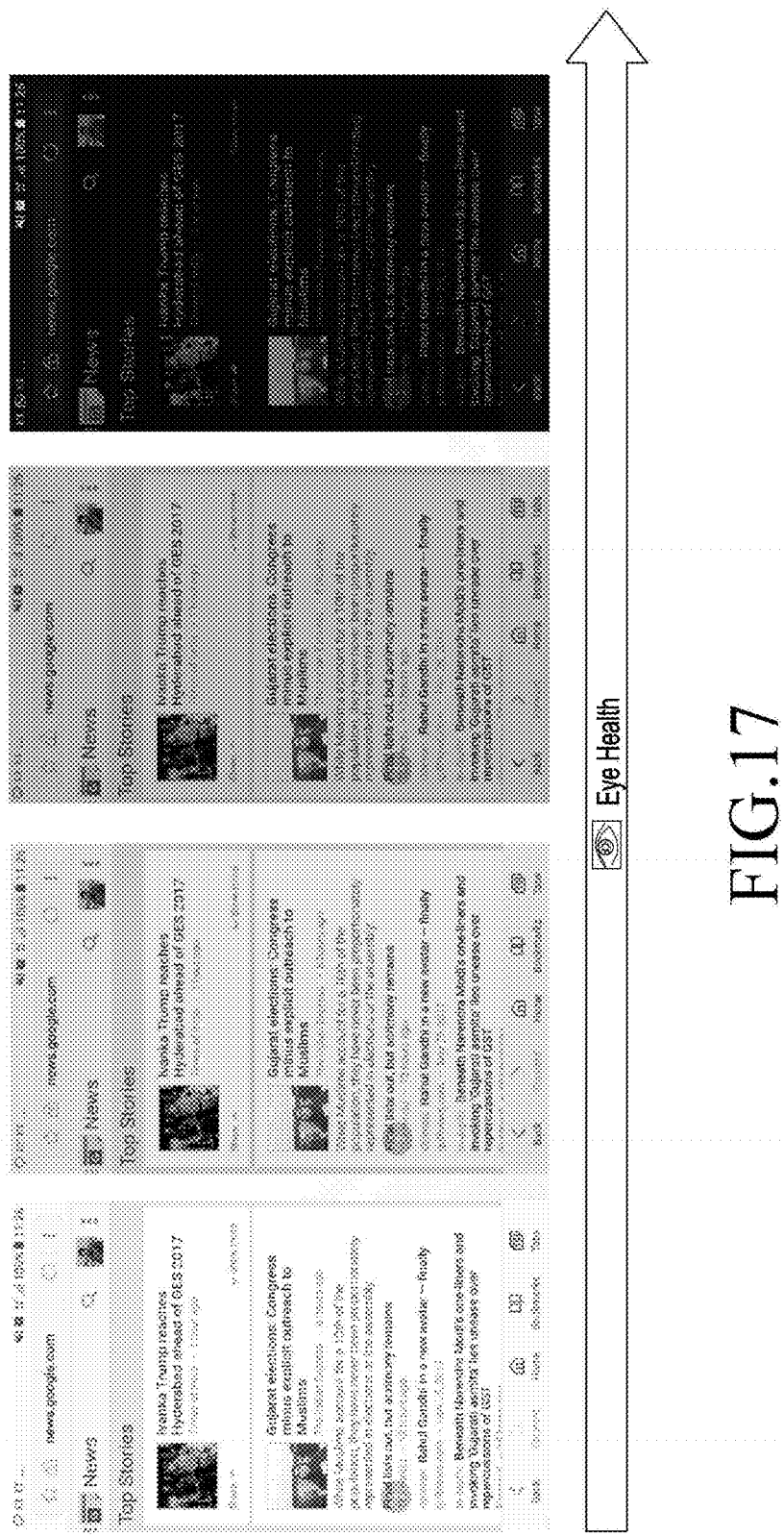
FIG. 17 illustrates an example use case for adapting content colors based on an eye health index, according to embodiments as disclosed herein.

FIG. 17 illustrates an example use case for adapting the content colors based on the eye health index, according to embodiments as disclosed herein. The display processor 104a can transform the colors of the text (present in the content) and background depending on the eye health index. In an example herein, based on the eye health index, the display processor 104a can transform the colors of the text and background as illustrated in FIG. 17 for placing on the display 104. In an embodiment, the display processor 104a can transform the colors of the text towards red. The insensitivity of rods to red light has led to the use of red lights under certain special circumstances; for example in the control rooms of submarines, in research laboratories, aircraft or during naked-eye astronomy as it does not require change in the eye adaption.

Figure 18:
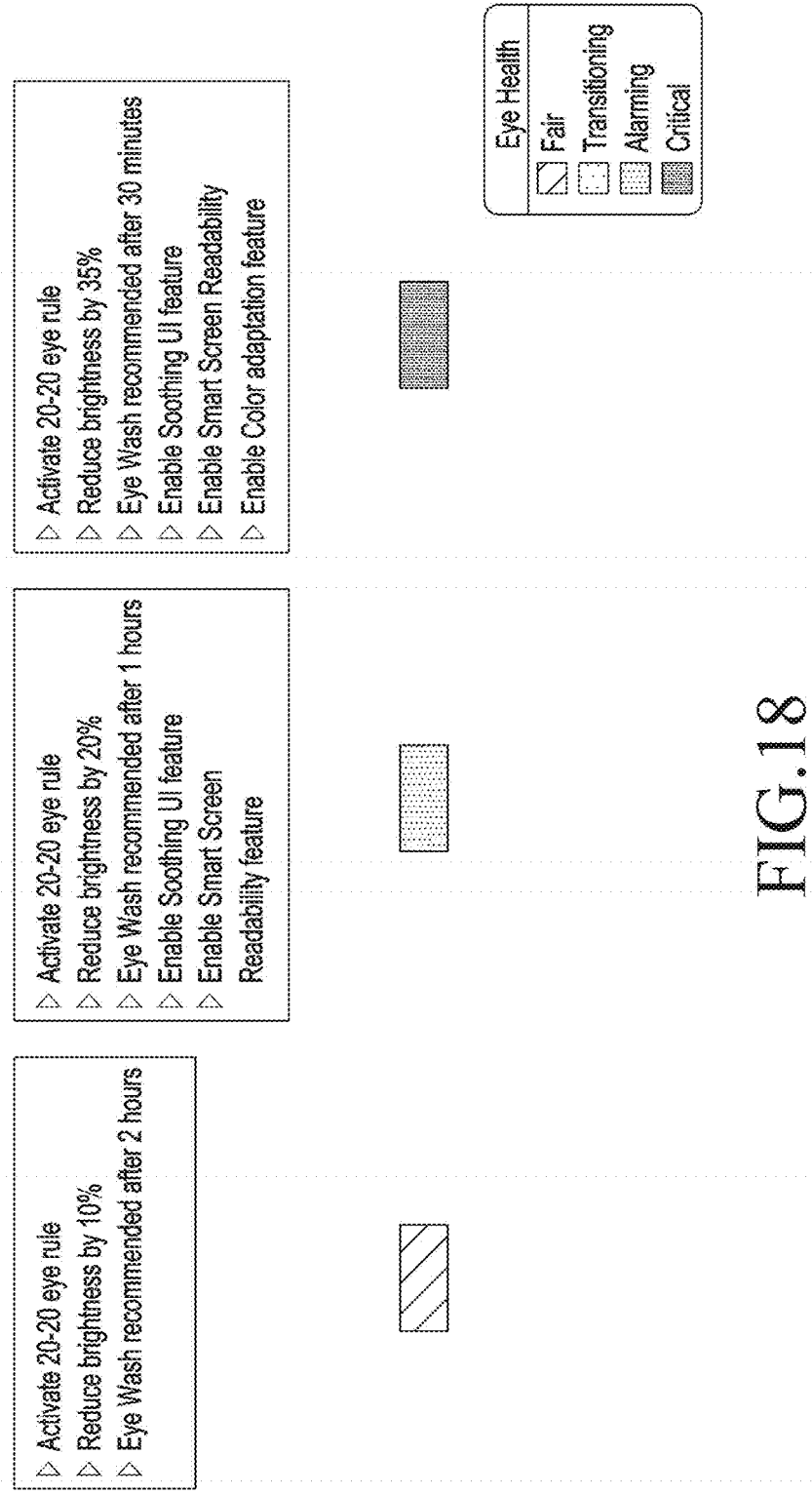
FIG. 18 illustrates an example use case for providing suggestions to a user based on an eye health index, according to embodiments as disclosed herein.

FIG. 18 illustrates an example use case for providing the suggestions to the user based on the eye health index, according to embodiments as disclosed herein. On determining that the eye health index of the user is transitioning, the recommendation module 110 can provide suggestions like, but not limited to, a suggestion for activating 20-20 eye rule (taking 20 seconds break for every 20 minutes and focusing eyes on something at least 20 feet away), a suggestion for reducing brightness by at least some amount (for example 10%), a suggestion for eye wash after 2 hours and so on.

On determining that the eye health index of the user is alarming, the recommendation module 110 can provide the suggestions like, but not limited to, a suggestion for activating 20-20 eye rule, a suggestion for reducing brightness by at least 20%, a suggestion for eye wash after 1 hour and so on. In addition, on determining that the eye health index of the user is alarming, the display processor 104a can enable the soothing UI feature and a smart screen readability feature (as illustrated in FIG. 20) or the like on the electronic device 100.

On determining that the eye health index of the user is critical, the recommendation module 110 can provide the suggestions like, but not limited to, a suggestion for activating 20-20 eye rule, a suggestion for reducing brightness by at least 35%, a suggestion for eye wash after 30 minutes and so on. In addition, on determining that the eye health index of the user is critical, the display module 104 can enable the soothing UI feature and the smart screen readability feature (as illustrated in FIG. 20), enable the content color adaption feature (as illustrated in FIG. 17) or the like on the electronic device 100.

Figure 19:
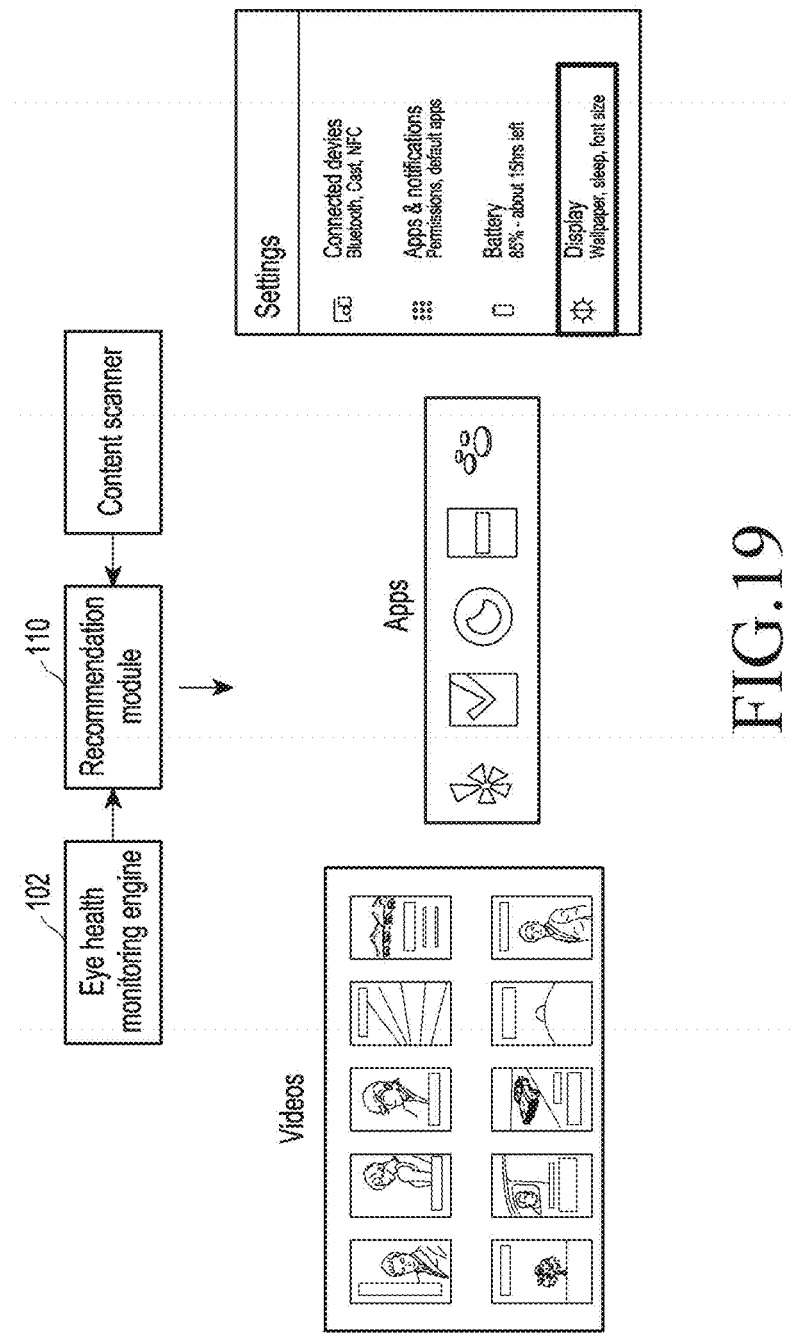
FIG. 19 is an example diagram illustrating providing of recommendations to a user based on an eye health index, according to embodiments as disclosed herein.

FIG. 19 is an example diagram illustrating providing of the recommendations to the user based on an eye health index, according to embodiments as disclosed herein. As illustrated in FIG. 19, the eye health-monitoring engine 102 scans the contents (stored in the memory or being accessed from the server/databases, one or more electronic devices and so on) and estimates the prospective eyestrain. Based on the estimated prospective eye strain and current eye health status, the recommendation module 110 can recommend appropriate videos, applications, settings (brightness, wallpaper and so on) and so on to the user.

Figure 20:
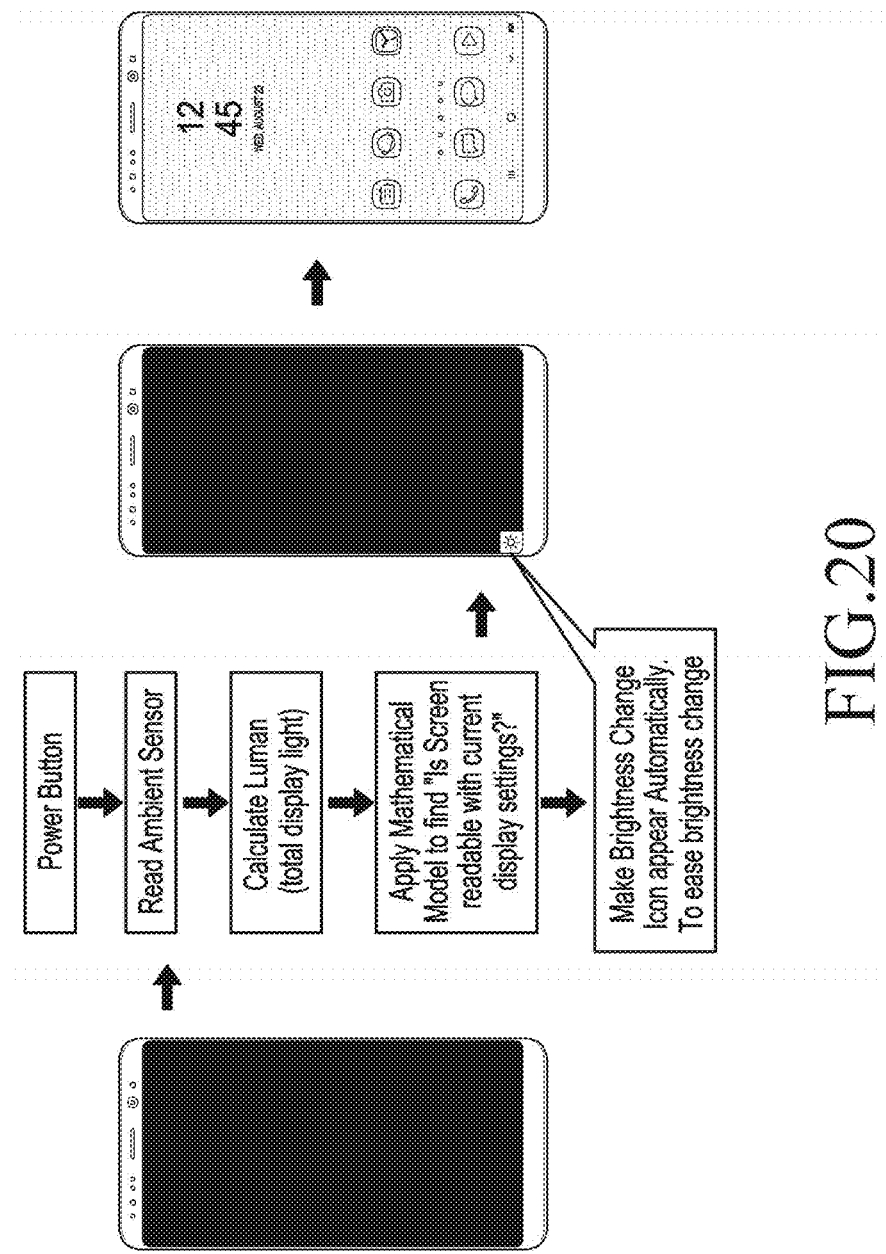
FIG. 20 is an example use case illustrating improvement of smart screen readability, according to embodiments as disclosed herein.

FIG. 20 is an example user case illustrating improvement of the smart screen readability, according to embodiments as disclosed herein. The user may face difficulty in high sunlight in changing brightness if an auto brightness mode was turned OFF on the electronic device 100. Thus, the eye health-monitoring engine 102 collects the data from the ambient sensor and calculates the total displayed light. Based on the total displayed light, the eye health-monitoring engine 102 checks whether the screen can be readable with the current display settings. On determining that the screen is not readable with the current display settings, the eye health-monitoring engine 102 instructs the display processor 104b to place the brightness change icon on the display which further displays the brightness change icon with high contrast. Thus, power consumption can be reduced and user's convenience of manual brightness settings can be protected.

The embodiments disclosed herein can be implemented through at least one software program running on at least one hardware device and performing network management functions to control the elements. The elements shown in FIG. 1 and FIG. 2 can be at least one of a hardware device, or a combination of hardware device and software module.

The embodiments disclosed herein describe methods and systems for monitoring health of eyes of the user. Therefore, it is understood that the scope of the protection is extended to such a program and in addition to a computer readable means having a message therein, such computer readable storage means contain program code means for implementation of one or more steps of the method, when the program runs on a server or mobile device or any suitable programmable device. The method is implemented in a preferred embodiment through or together with a software program written in e.g. Very high speed integrated circuit Hardware Description Language (VHDL) another programming language, or implemented by one or more VHDL or several software modules being executed on at least one hardware device. The hardware device can be any kind of portable device that can be programmed. The device may also include means which could be e.g. hardware means like e.g. an ASIC, or a combination of hardware and software means, e.g. an ASIC and an FPGA, or at least one microprocessor and at least one memory with software modules located therein. The method embodiments described herein could be implemented partly in hardware and partly in software. Alternatively, the invention may be implemented on different hardware devices, e.g. using a plurality of CPUs.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of embodiments, those skilled in the art will recognize that the embodiments herein can be practiced with modification within the spirit and scope of the embodiments as described herein.

What is claimed is:

1. A method for monitoring health of eyes of a user of an electronic device performed by at least one processor of the electronic device, the method comprising:
   identifying an ambient light level around the electronic device; and
   while the identified ambient light level is below a first threshold:
      identifying a lumen output of at least one content displayed on a display of the electronic device for an interval;
      identifying a variation in a pupil size of the user by using a first model for estimating the variation in the pupil size of the user based on inputs of the first model, wherein the inputs of the first model include the identified lumen output and at least one user profile;
      generating an eye health index for the user using a second model which generates the eye health index for the user based on evaluating the at least one user profile, the lumen output of the at least one content, and at least one activity of the user with respect to the identified variation in the pupil size of the user; and
      controlling a brightness setting of the display according to the eye health index for the user.

2. The method of claim 1, wherein identifying the lumen output of the at least one content to be displayed includes:
   identifying a luminance of the at least one content and a backlight level; and
   identifying the lumen output of the at least one content based on a relation between the luminance of the at least one content to be displayed and the backlight level.

3. The method of claim 2, wherein the lumen output of the at least one content indicates a total light to be emitted from the display and a corresponding luminance variance.

4. The method of claim 2, wherein the relation between the luminance of the at least one content and the backlight level is identified as at least a part of a lumen model based on machine learning.

5. The method of claim 1, further comprising:
based on identifying that the ambient light level is below a second threshold, displaying at least one tag corresponding to each of the at least one content based on the eye health index,
wherein the at least one tag includes at least one of a safe tag, an unsafe tag, and a range tag.

6. The method of claim 1, further comprising displaying, on the display, at least one recommendation regarding display settings based on the eye health index for the user.

7. The method of claim 1, further comprising:
based on identifying a change in the at least one content, identifying a new eye health index; and
displaying, on the display, the at least one content according to the new eye health index.

8. An electronic device for monitoring health of eyes of a user, the electronic device comprising:
a display; and
at least one processor configured to:
identify an ambient light level around the electronic device; and
while the identified ambient light level is below a first threshold:
identify a lumen output of at least one content displayed on the display for an interval;
identify a variation in a pupil size of the user by using a first model for estimating the variation in the pupil size of the user based on inputs of the first model, wherein the inputs of the first model include the identified lumen output and at least one user profile;
provide an eye health index for the user using a second model which generates the eye health index for the user based on evaluating the at least one user profile, the lumen output of the at least one content, and at least one activity of the user with respect to the identified variation in the pupil size of the user; and
control a brightness setting of the display according to the eye health index for the user.

9. The electronic device of claim 8, wherein the at least one processor is further configured to:
identify a luminance of the at least one content and a backlight level; and
identify the lumen output of the at least one content based on a relation between the luminance of the at least one content and the backlight level.

10. The electronic device of claim 9, wherein the lumen output of the at least one content indicates a total light to be emitted from the display and a corresponding luminance variance.

11. The electronic device of claim 9, wherein the relation between the luminance of the at least one content and the backlight level is identified as at least a part of a lumen model based on machine learning.

12. The electronic device of claim 8, wherein the variation in the pupil size of the user is identified based on a Holladay formula.

13. The electronic device of claim 8, wherein the second model is identified based on hierarchical regression modeling.

14. The electronic device of claim 8, wherein the at least one processor is further configured to:
based on identifying that the ambient light level is below a second threshold, display at least one tag corresponding to each of the at least one content based on the eye health index for the user,
wherein the at least one tag includes at least one of a safe tag, an unsafe tag, and a range tag.

15. The electronic device of claim 8, wherein the at least one processor is further configured to display, on the display, at least one recommendation regarding display settings based on the eye health index for the user.

16. The electronic device of claim 8, wherein the at least one processor is further configured to:
based on identifying a change in the at least one content, identify a new eye health index; and
display, on the display, the at least one content according to the new eye health index.

17. The electronic device of claim 8, wherein the interval is variable.

* * * * *